US012592304B2

(12) United States Patent
Hermey et al.

(10) Patent No.: US 12,592,304 B2
(45) Date of Patent: **\*Mar. 31, 2026**

(54) RULES-BASED PROCESSING OF STRUCTURED DATA

(71) Applicant: Managed Health Care Associates, Inc., Florham Park, NJ (US)

(72) Inventors: Thomas J. Hermey, Boonton, NJ (US); Tillman E. Johnson, Chapin, SC (US); Jhanvika Thakkar, Bridgewater, NJ (US); Timothy R. Tannert, Gibsonia, PA (US); Shantanu V. Bhide, Sewickley, PA (US); Shirin Vinayak, Short Hills, NJ (US); Glen R. McCloskey, Springfield Township, NJ (US); Neelanjana Panda, Jersey City, NJ (US); Milind Deodhar, Parsippany, NJ (US); Rene' Charlene Bloemke, Woodland, WA (US)

(73) Assignee: MANAGED HEALTH CARE ASSOCIATES, INC., Parsippany, NJ (US)

( \* ) Notice: Subject to any disclaimer, the term of this patent is extended or adjusted under 35 U.S.C. 154(b) by 25 days.

This patent is subject to a terminal disclaimer.

(21) Appl. No.: 18/884,723

(22) Filed: Sep. 13, 2024

(65) Prior Publication Data

US 2025/0087327 A1     Mar. 13, 2025

Related U.S. Application Data

(63) Continuation of application No. 17/085,631, filed on Oct. 30, 2020, now Pat. No. 12,094,588.

(Continued)

(51) Int. Cl.
*G16H 20/10* (2018.01)
*G06F 9/54* (2006.01)

(Continued)

(52) U.S. Cl.
CPC ............. *G16H 20/10* (2018.01); *G06F 9/547* (2013.01); *G06F 16/258* (2019.01); *G06N 20/00* (2019.01)

(58) Field of Classification Search
CPC ........ G16H 20/10; G16H 10/60; G16H 50/20; G06F 9/547; G06F 16/258; G06N 20/00
See application file for complete search history.

(56) References Cited

U.S. PATENT DOCUMENTS 7,111,780 B2     9/2006   Broussard et al.
7,438,218 B2     10/2008   Dooley et al.
(Continued)

FOREIGN PATENT DOCUMENTS

CA          2482370          4/2019

*Primary Examiner* — Jason S Tiedeman

(74) *Attorney, Agent, or Firm* — Fish & Richardson P.C.

(57) ABSTRACT

A rules processing system includes one or more processors and one or more memory devices storing non-transitory, computer-readable instructions that, when executed by the one or more processors, cause the one or more processors to perform operations. The operations include receiving, by an API gateway, a transaction from a pharmacy, the transaction having a first data format; reformatting, by a translation component, the transaction received by the API gateway into a structured data format used by a rules engine included in the rules processing system; evaluating, by the rules engine, one or more of fields of the transaction according to a configurable set of logic rules; inserting, into a wrapper of the transaction, supplementary data based on the evaluation of the one or more fields; reformatting, by the translation component, the transaction into the first data format; and transmitting, by the API gateway, the transaction to the pharmacy.

20 Claims, 21 Drawing Sheets

Related U.S. Application Data

(60) Provisional application No. 62/929,231, filed on Nov. 1, 2019.

(51) Int. Cl.
    *G06F 16/25*       (2019.01)
    *G06N 20/00*     (2019.01)

(56)           References Cited

U.S. PATENT DOCUMENTS

| | | | |
|---|---|---|---|
| 7,711,660 B1 | 5/2010 | Gentile et al. | |
| 7,797,172 B2 | 9/2010 | Fitzgerald et al. | |
| 7,926,709 B1 | 4/2011 | Dooley et al. | |
| 8,190,453 B2 | 5/2012 | Rowe et al. | |
| 8,457,992 B1 | 6/2013 | Harding et al. | |
| 8,489,411 B1 | 7/2013 | Rowe et al. | |
| 8,515,784 B2 | 8/2013 | Russell et al. | |
| 8,595,206 B1 | 11/2013 | Ansari et al. | |
| 10,331,855 B1 | 6/2019 | Bratton et al. | |
| 10,417,380 B1 | 9/2019 | Kaye et al. | |
| 10,678,615 B1 | 6/2020 | Creighton et al. | |
| 11,456,065 B1 | 9/2022 | Ansari et al. | |
| 12,229,833 B1 * | 2/2025 | Draa | G06Q 10/10 |
| 2002/0040282 A1 | 4/2002 | Bailey et al. | |
| 2004/0006490 A1 | 1/2004 | Gingrich et al. | |
| 2004/0138921 A1 | 7/2004 | Broussard et al. | |
| 2006/0149587 A1 | 7/2006 | Hill et al. | |
| 2007/0088458 A1 | 4/2007 | Laughland et al. | |
| 2009/0080408 A1 * | 3/2009 | Natoli | G06F 16/258 370/351 |
| 2009/0254368 A1 | 10/2009 | Cunnold | |
| 2009/0327363 A1 | 12/2009 | Cullen et al. | |
| 2011/0307270 A1 | 12/2011 | Berkelhamer et al. | |
| 2012/0035957 A1 | 2/2012 | Hanz et al. | |
| 2013/0041888 A1 | 2/2013 | Eisner et al. | |
| 2013/0173719 A1 | 7/2013 | Ahmed et al. | |
| 2014/0095417 A1 | 4/2014 | Herz et al. | |
| 2014/0282197 A1 | 9/2014 | Keefe et al. | |
| 2015/0206262 A1 | 7/2015 | Pinsonneault et al. | |
| 2015/0278469 A1 | 10/2015 | Kahlon et al. | |
| 2015/0371000 A1 | 12/2015 | Pinsonneault | |
| 2015/0371001 A1 | 12/2015 | Pinsonneault et al. | |
| 2016/0019354 A1 | 1/2016 | Grant et al. | |
| 2016/0163034 A1 | 6/2016 | Jacobs et al. | |
| 2016/0350480 A1 | 12/2016 | Gerdeman et al. | |
| 2017/0065488 A1 | 3/2017 | Thach et al. | |
| 2017/0068798 A1 | 3/2017 | Akinwale et al. | |
| 2017/0076058 A1 | 3/2017 | Stong | |
| 2017/0177829 A1 | 6/2017 | Wilkinson et al. | |
| 2017/0300655 A1 | 10/2017 | Lane et al. | |
| 2018/0121620 A1 | 5/2018 | Bastide et al. | |
| 2019/0115100 A1 | 4/2019 | Madonna et al. | |
| 2019/0139636 A1 * | 5/2019 | Chandrasekaran | G16H 70/40 |
| 2019/0304021 A1 | 10/2019 | Rutherford et al. | |
| 2019/0384849 A1 | 12/2019 | Sundararaman et al. | |
| 2020/0058381 A1 | 2/2020 | Patel | |
| 2020/0137043 A1 | 4/2020 | Cirillo | |
| 2020/0294633 A1 | 9/2020 | Namboodiri | G06F 16/88 |
| 2021/0134098 A1 | 5/2021 | Sauer et al. | |
| 2021/0225473 A1 | 7/2021 | Hong et al. | |

* cited by examiner

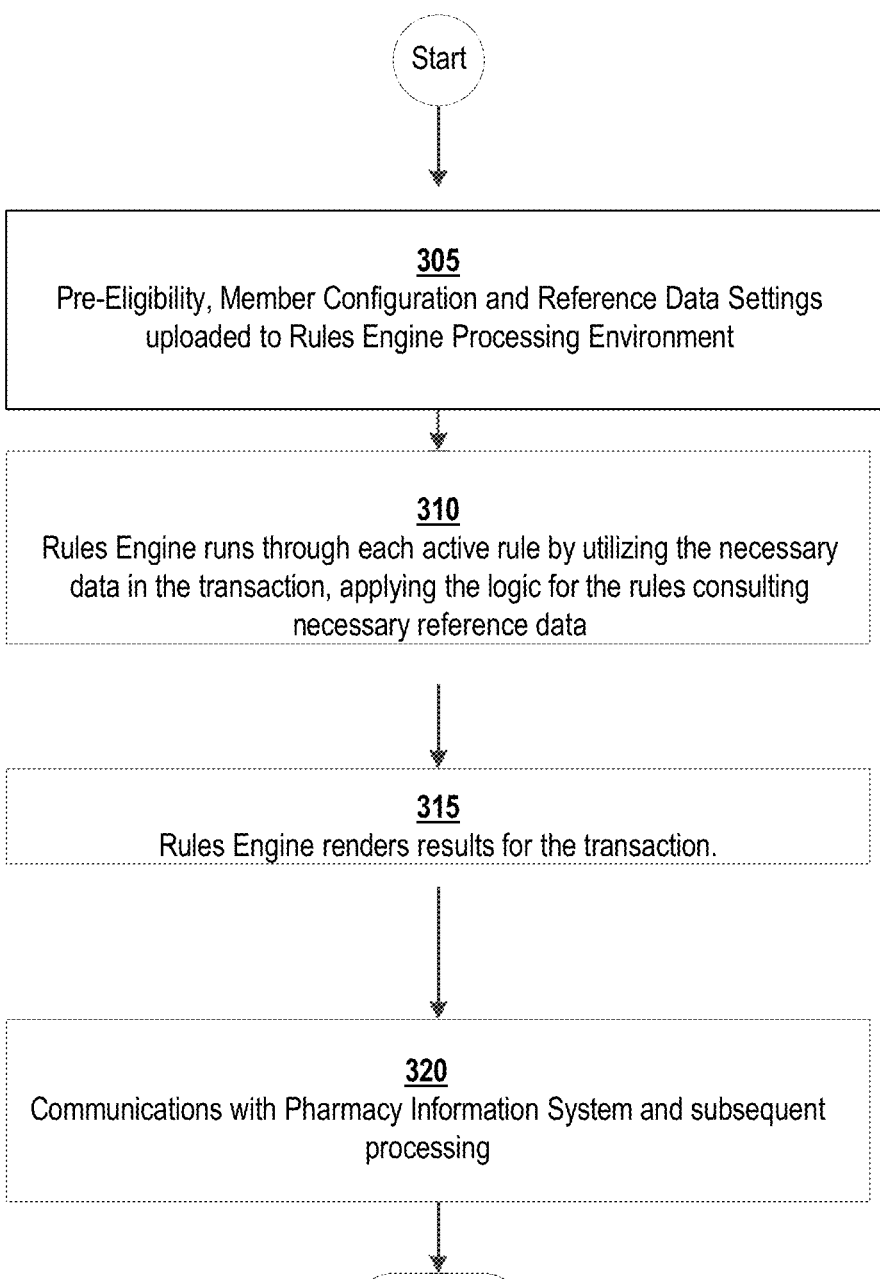

Start

305
Pre-Eligibility, Member Configuration and Reference Data Settings uploaded to Rules Engine Processing Environment

310
Rules Engine runs through each active rule by utilizing the necessary data in the transaction, applying the logic for the rules consulting necessary reference data

315
Rules Engine renders results for the transaction.

320
Communications with Pharmacy Information System and subsequent processing End

*Fig. 3*

Start

800

Translator receives
transaction and determines
format based on wrapper
information

802

Fetches translation metadata
for identified format from
database

804

Runs translator engine and
converts received format to
Rules Engine recognizable
format

808

Sends translated transaction to
Rules Engine for
processing

Start

900 — Rules Engine receives transaction and writes it back to managed cache

902 — Rules Engine applies rules and writes the modified version of transaction back to managed cache 904 — Managed Cache downloads nightly to on-prem storage 906 — Reports generated from On Prem storage

*Fig. 11*

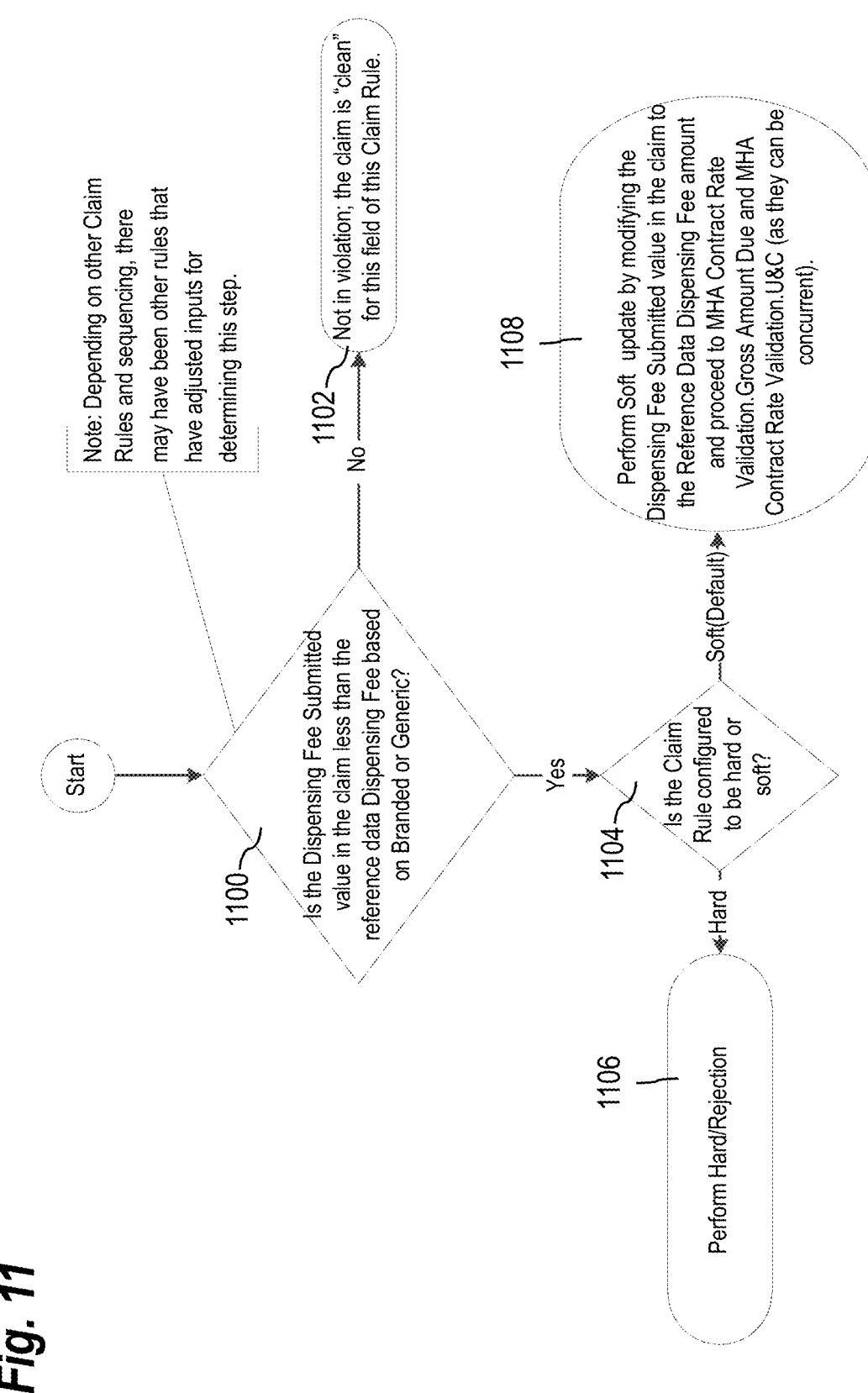

Start

1100 — Is the Dispensing Fee Submitted value in the claim less than the reference data Dispensing Fee based on Branded or Generic?

Note: Depending on other Claim Rules and sequencing, there may have been other rules that have adjusted inputs for determining this step.

No → 1102 — Not in violation; the claim is "clean" for this field of this Claim Rule.

Yes → 1104 — Is the Claim Rule configured to be hard or soft?

Hard → 1106 — Perform Hard/Rejection

Soft(Default) → 1108 — Perform Soft update by modifying the Dispensing Fee Submitted value in the claim to the Reference Data Dispensing Fee amount and proceed to MHA Contract Rate Validation.Gross Amount Due and MHA Contract Rate Validation.U&C (as they can be concurrent).

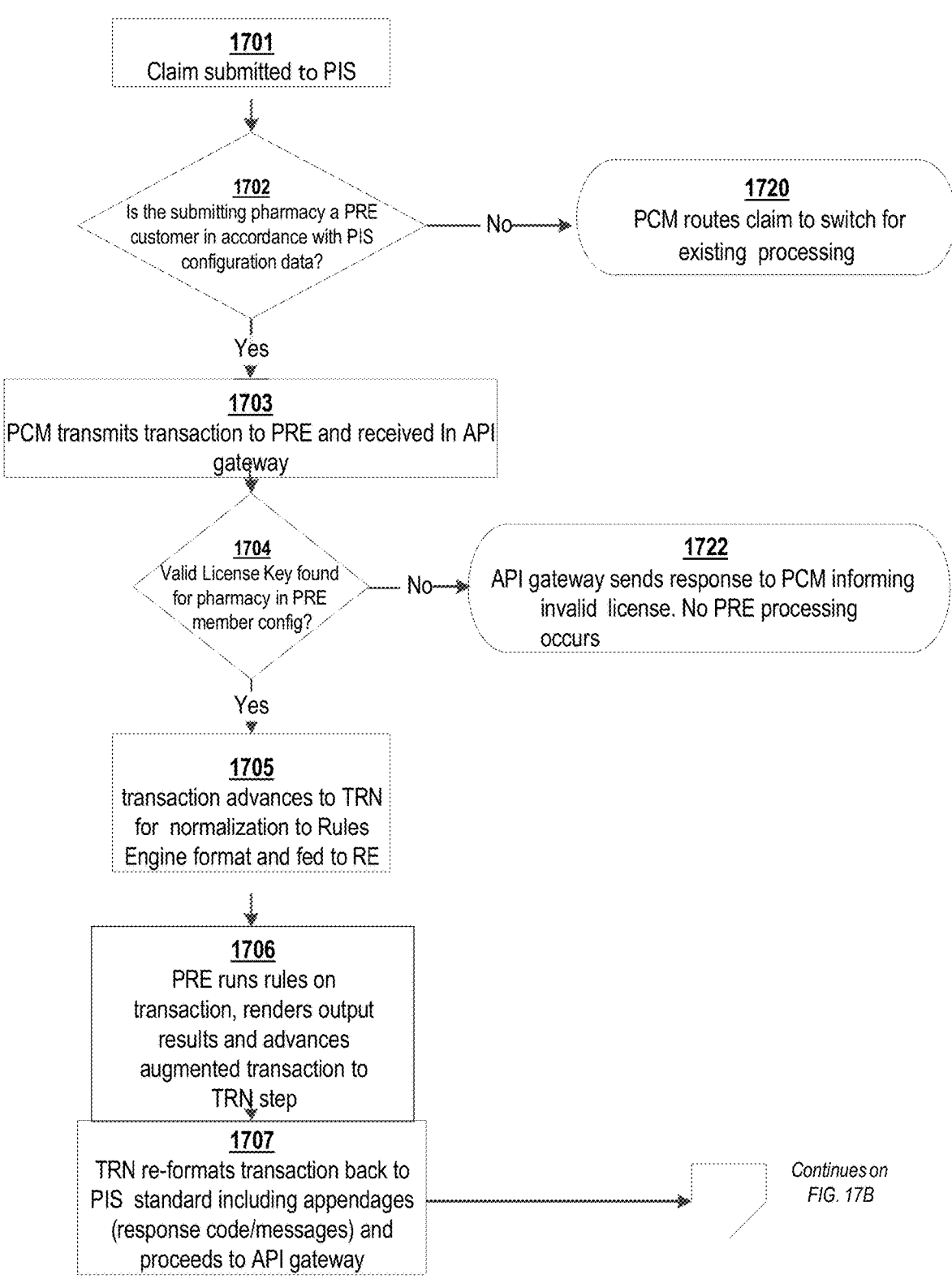

1701
Claim submitted to PIS

1702
Is the submitting pharmacy a PRE customer in accordance with PIS configuration data?

— No →

1720
PCM routes claim to switch for existing processing

Yes

1703
PCM transmits transaction to PRE and received In API gateway

1704
Valid License Key found for pharmacy in PRE member config?

— No →

1722
API gateway sends response to PCM informing invalid license. No PRE processing occurs Yes

1705
transaction advances to TRN for normalization to Rules Engine format and fed to RE

1706
PRE runs rules on transaction, renders output results and advances augmented transaction to TRN step

1707
TRN re-formats transaction back to PIS standard including appendages (response code/messages) and proceeds to API gateway Continues on
FIG. 17B

*Fig. 17A*

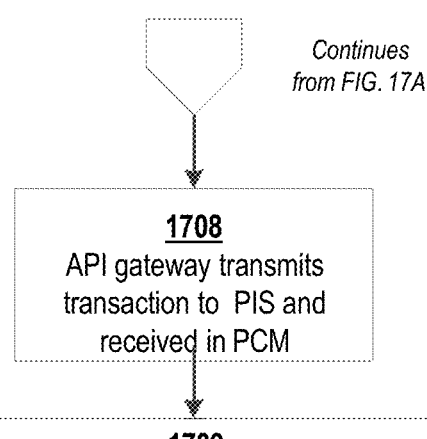

*Continues
from FIG. 17A*

1708
API gateway transmits
transaction to PIS and
received in PCM

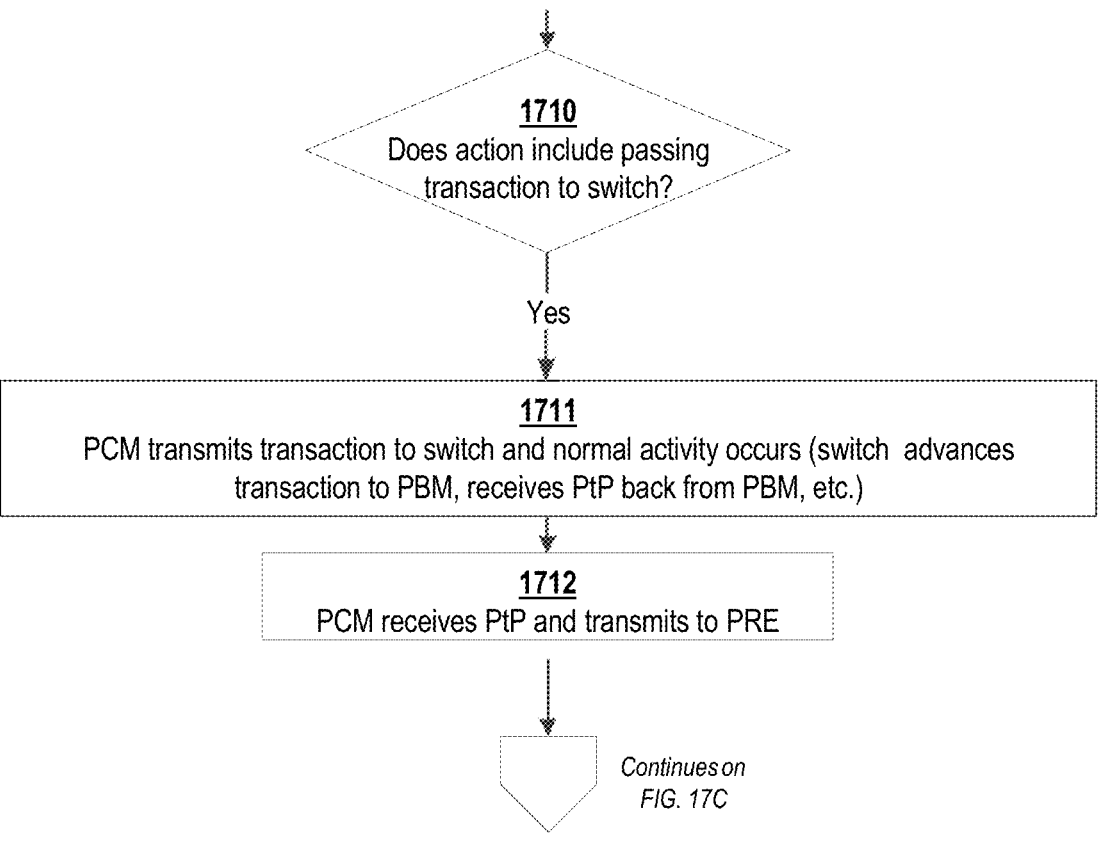

1709
PIS executes appropriate subsequent action(s) advised from RE which could include one or
more of:
- Notify Pharmacy Technician why transaction is rejected or has been augmented
- Pass augmented transaction to switch
- Update PIS Configuration data
- Update certain reference data

1710
Does action include passing
transaction to switch?

Yes

1711
PCM transmits transaction to switch and normal activity occurs (switch advances
transaction to PBM, receives PtP back from PBM, etc.)

1712
PCM receives PtP and transmits to PRE

*Continues on
FIG. 17C*

*Fig. 17B*

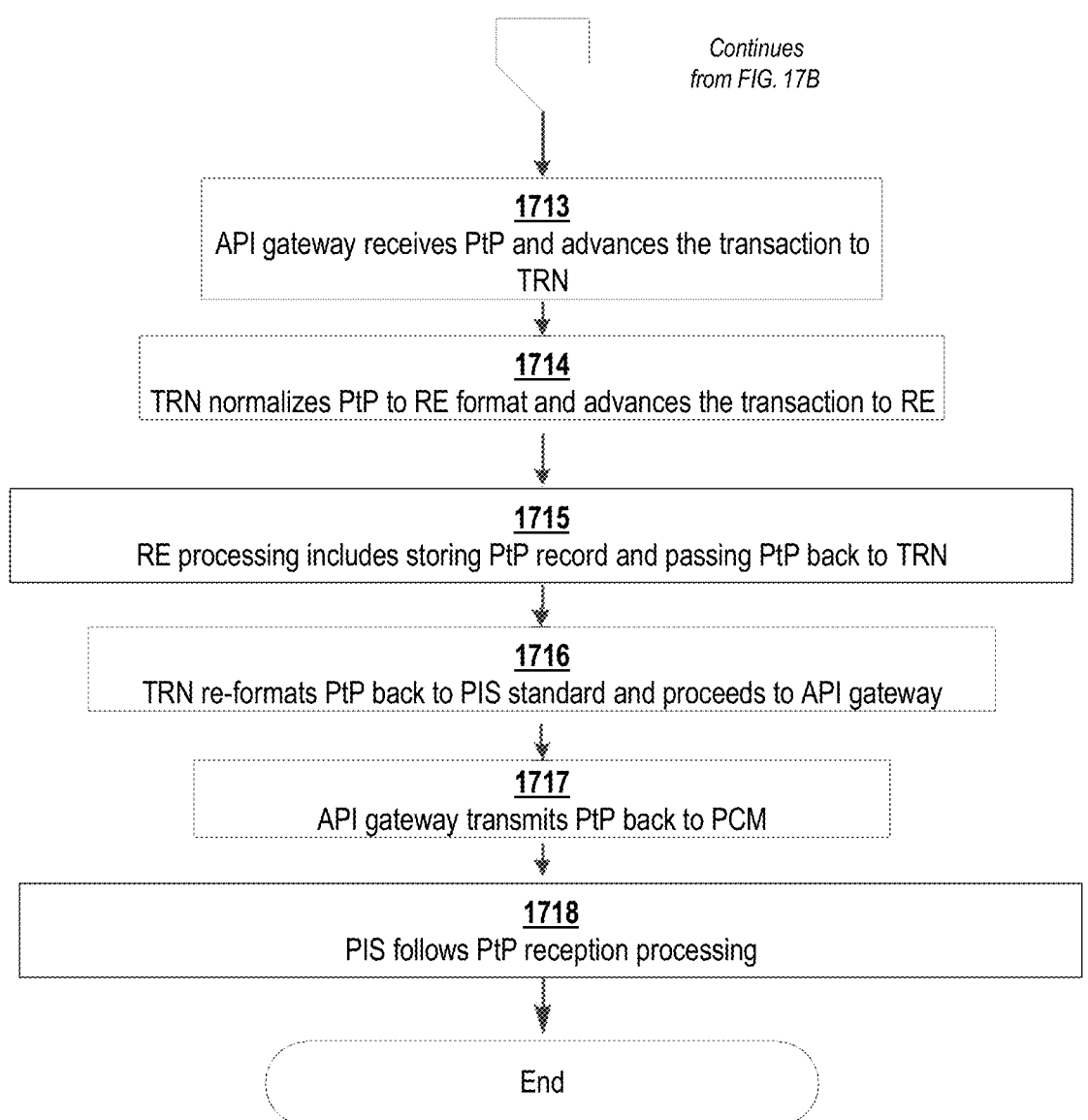

*Continues
from FIG. 17B*

1713
API gateway receives PtP and advances the transaction to TRN

1714
TRN normalizes PtP to RE format and advances the transaction to RE

1715
RE processing includes storing PtP record and passing PtP back to TRN

1716
TRN re-formats PtP back to PIS standard and proceeds to API gateway

1717
API gateway transmits PtP back to PCM

1718
PIS follows PtP reception processing

End

*Fig. 17C*

RULES-BASED PROCESSING OF STRUCTURED DATA

CROSS-REFERENCE TO RELATED APPLICATIONS

This application is a continuation application of and claims priority to U.S. patent application Ser. No. 17/085,631, filed on Oct. 30, 2020, which claims the benefit of priority to U.S. Provisional Patent Application No. 62/929,231, filed Nov. 1, 2019. The entire disclosures of each of the foregoing applications are incorporated herein by reference.

FIELD OF THE TECHNOLOGY

The present disclosure relates generally to processing of structured pharmacy data.

BACKGROUND

Generally, the pharmacy billing cycle is as follows. A pharmacy receives a prescription request and the prescription is stored in a pharmacy information system (PIS). The prescription request may be received, for example, via paper, telephone, or fax, and the information is entered into the PIS manually by a user. Alternatively an "e-prescription" may be transmitted from a computer system at the requesting facility to the PIS through a computer network of connections and associated services. Aside from the prescription itself, various additional or missing data may be entered into the PIS including, without limitation, prescriber information; applicable billing information (e.g., insurance information, copay); patient information; or drug information (e.g., the medication's National Drug Code).

Once the information is in the PIS, the PIS encodes the entered information to create a claim transaction (sometimes referred to as a claim or as a transaction) that includes various data fields. The PIS sends the claim transaction to a switch vendor in a format that complies with various standards, e.g., as defined by the National Council for Prescription Drug Programs (NCPDP). At this stage, the switch vendor can reject the claim due to missing or invalid fields (e.g., bank identification number, day's supply, prescriber identifier, or other data fields).

If the switch vendor does not reject the transaction, the claim is adjudicated by a third party payor that handles the financing of the prescription. Even if all fields are present and valid, a claim may still be rejected, for example, if the patient's age exceeds a maximum age for a benefit, if a prescribed product or service is not covered by benefits, or if a prescription is being refilled too soon. This level of rejection is typically from the payor's adjudication engine. If the claim is not rejected, the payor determines the patient's benefit plan coverage, e.g., which indicates how much the patient owes for the prescription. This information is then returned to the PIS, and the pharmacy fills the prescription and dispenses it to the patient. Note that pharmacies sometimes fill prescription claims for which they do not generate electronic claims and for which they do not follow the transaction process described above.

In some cases, pharmacies follow a "fill and bill" model, in which a prescription is first filled and then billing occurs. In some cases, the pharmacy support industry follows a "bill and fill" model, in which billing is performed before the prescription is filled. "Fill and bill" refers to filling the prescription before performing billing. With connected systems and first-to-bill-gets-paid logic, pharmacies are adopting a "bill and fill" approach. In some cases, there may be findings post-adjudication, such as after a transaction has been transmitted through a switch provider to a pharmacy benefit manager, indicating that the original submission should have contained a different value for each of one or more certain data fields of the claim. In such cases, the pharmacy can reverse and re-submit the affected claim(s), e.g., using updated data values.

SUMMARY

This description relates to methods, systems, and apparatuses related to rules-based processing of structured pharmacy data.

According to some embodiments, this disclosure describes a rules processing system including one or more processors, and one or more memory devices storing non-transitory, computer-readable instructions that, when executed by the one or more processors, cause the one or more processors to perform operations. The operations include receiving, by an application program interface (API) gateway, a transaction from a pharmacy, the transaction having a first data format; validating, by the API gateway, that the pharmacy is authorized to access the rules processing system; reformatting, by a translation component, the transaction received by the API gateway into a structured data format used by a rules engine included in the rules processing system; evaluating, by the rules engine, one or more of fields of the transaction according to a configurable set of logic rules, including at least one of modifying values of the one or more fields, generating a rejection of the transaction, and generating an indication that at least some of the one or more fields do not violate the set of logic rules; inserting, into a wrapper of the transaction, supplementary data based on the evaluation of the one or more fields; reformatting, by the translation component, the transaction into the first data format, and transmitting, by the API gateway, the transaction to the pharmacy.

Embodiments can include any one or more of at least the following features.

Evaluating the one or more fields includes comparing a value in a first field of the one or more fields to a predetermined comparison value; determining, based on a result of comparing the value to the predetermined comparison value, that a logic rule in the set of logic rules dictates a change to the value; and changing the value in the first field to a modified value according to the logic rule.

The supplementary data includes an encoded instruction indicating one or more other operations to be performed by the pharmacy.

The operations include accessing stored data indicating a format for the encoded instruction based on the pharmacy from which the transaction is received; and generating the encoded instruction in the indicated format.

The wrapper has a second data format different from the first data format, and reformatting the transaction into the first data format includes retaining the wrapper in the second data format.

The operations include adding a new field to the wrapper; and inserting the supplementary data into the new field.

The logic rules depend upon a set of pharmacy-specific parameters.

The rules processing system includes a cloud-based system remote from the pharmacy, and the API gateway includes an internet-accessible API gateway.

The operations include comparing data in the transaction to stored data from one or more other transactions; based on the comparison, generating an indication that a clinical intervention is needed for a patient associated with the transaction; and including the indication in the supplementary data.

The operations include applying a machine learning model to data in the transaction and to data included in one or more other transactions from one or more other pharmacies, to generate an outbreak prediction indicating a predicted disease outbreak; and including the outbreak prediction in the supplementary data.

This disclosure also describes methods. In some embodiments, this disclosure describes a computer-implemented method for transaction processing by a rules processing system. The method includes receiving, by an application program interface (API) gateway, a transaction from a pharmacy, the transaction having a first data format; validating, by the API gateway, that the pharmacy is authorized to access the rules processing system; reformatting, by a translation component, the transaction received by the API gateway into a structured data format used by a rules engine included in the rules processing system; evaluating, by the rules engine, one or more of fields of the transaction according to a configurable set of logic rules, including at least one of modifying values of the one or more fields, generating a rejection of the transaction, and generating an indication that at least some of the one or more fields do not violate the set of logic rules; inserting, into a wrapper of the transaction, supplementary data based on the evaluation of the one or more fields; reformatting, by the translation component, the transaction into the first data format, and transmitting, by the API gateway, the transaction to the pharmacy.

Embodiments can include any one or more of at least the following features.

Evaluating the one or more fields includes comparing a value in a first field of the one or more fields to a predetermined comparison value; determining, based on a result of comparing the value to the predetermined comparison value, that a logic rule in the set of logic rules dictates a change to the value; and changing the value in the first field to a modified value according to the logic rule.

The supplementary data includes an encoded instruction indicating one or more other operations to be performed by the pharmacy.

The method includes accessing stored data indicating a format for the encoded instruction based on the pharmacy from which the transaction is received; and generating the encoded instruction in the indicated format.

The wrapper has a second data format different from the first data format, and reformatting the transaction into the first data format includes retaining the wrapper in the second data format.

The method includes adding a new field to the wrapper; and inserting the supplementary data into the new field.

This disclosure also describes storage media. In some embodiments, this disclosure describes a non-transitory, computer-readable medium storing instructions that, when executed by a computer system, cause the computer system to perform operations for transaction processing by a rules processing system. The operations include receiving, by an application program interface (API) gateway, a transaction from a pharmacy, the transaction having a first data format; validating, by the API gateway, that the pharmacy is authorized to access the rules processing system; reformatting, by a translation component, the transaction received by the API gateway into a structured data format used by a rules engine included in the rules processing system; evaluating, by the rules engine, one or more of fields of the transaction according to a configurable set of logic rules, including at least one of modifying values of the one or more fields, generating a rejection of the transaction, and generating an indication that at least some of the one or more fields do not violate the set of logic rules; inserting, into a wrapper of the transaction, supplementary data based on the evaluation of the one or more fields; reformatting, by the translation component, the transaction into the first data format, and transmitting, by the API gateway, the transaction to the pharmacy.

Embodiments can include any one or more of at least the following features.

Evaluating the one or more fields includes comparing a value in a first field of the one or more fields to a predetermined comparison value; determining, based on a result of comparing the value to the predetermined comparison value, that a logic rule in the set of logic rules dictates a change to the value; and changing the value in the first field to a modified value according to the logic rule.

The supplementary data includes an encoded instruction indicating one or more other operations to be performed by the pharmacy.

The operations include accessing stored data indicating a format for the encoded instruction based on the pharmacy from which the transaction is received; and generating the encoded instruction in the indicated format.

The wrapper has a second data format different from the first data format, and reformatting the transaction into the first data format includes retaining the wrapper in the second data format.

The operations include adding a new field to the wrapper; and inserting the supplementary data into the new field.

Certain embodiments may provide one or more of the following advantages. The types and amounts of supplementary data included in results of transaction processing can be increased, while a desired format of the transaction can be maintained for compatibility with a source of the transaction. Encoded instructions based on transaction processing can be directly included in transaction wrappers to allow for efficient external processing of the instructions, reducing external processing burdens. Checks of transactions can reduce network transmission loads. Format conversion of transactions can increase processing speed, reduce a number of processing errors, or both. Use of a structured data format can allow for more efficient cross-comparisons and aggregations between data from different types of transactions. In the context of transactions that include pharmacy data, the sensitivity of detecting disease outbreaks based on pharmacy transactions can be increased. For pharmacy data, processing may result in, for example, higher and/or more accurate reimbursement rates, improved inventory management, and improved (e.g., more accurate) data records, for data records both internal to a pharmacy and sent externally.

The details of one or more implementations are set forth in the accompanying drawings and the description below. Other features and advantages will be apparent from the description and drawings, and from the claims.

BRIEF DESCRIPTION OF THE DRAWINGS

FIGS. 3-15 are flow charts.

FIGS. 17A-17C are flow charts.

DETAILED DESCRIPTION

Figure 1:
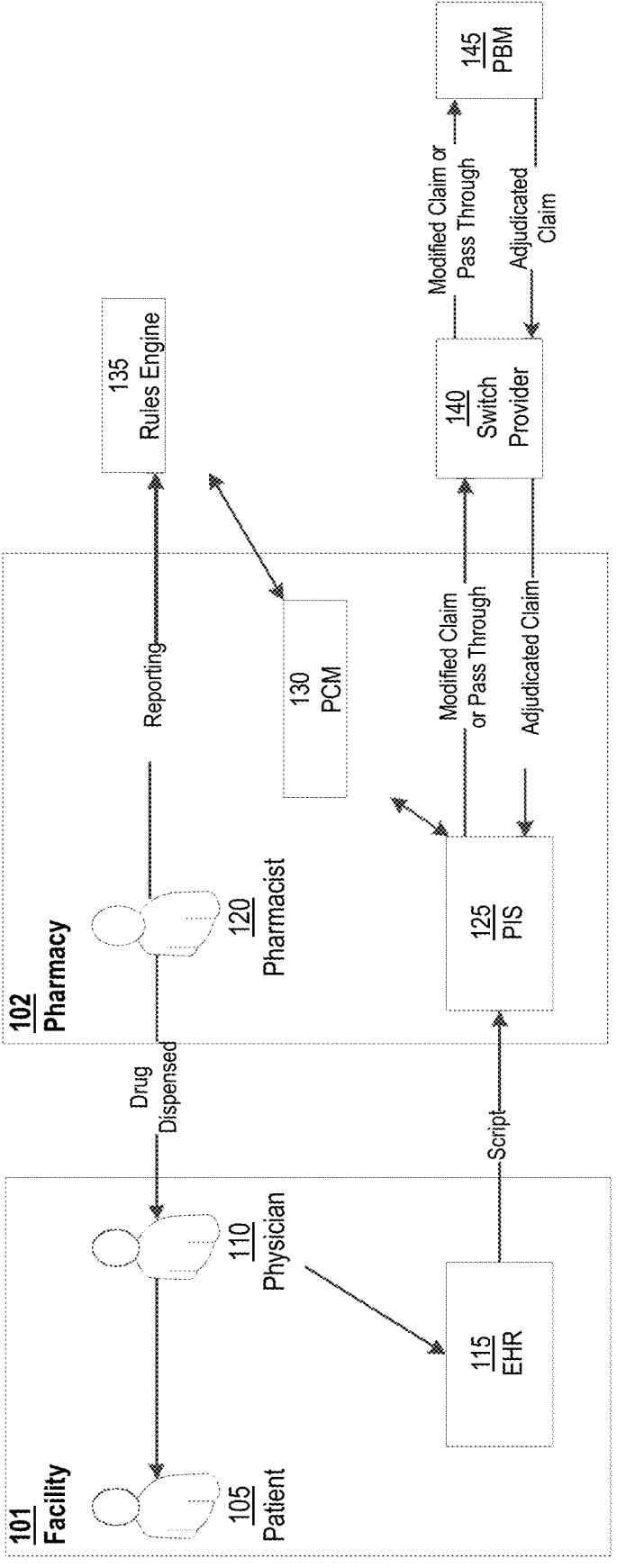
FIG. 1 is a block diagram showing an example system including a pharmacy and a rules engine.

We describe here a data analysis and modification system making use of structured data. Based on a source and/or type of an incoming transaction, the system converts the transaction into a structured, common format that allows for uniform processing, e.g., analysis and/or modification, by a rules engine. A wrapper of the transaction is used to embed supplementary data based on the analysis, e.g., by way of creation of an additional data field in the wrapper. Subsequent to processing by the rules engine, the transaction is re-formatted back into its original format or into another format, while data added to the wrapper is included when the transaction is returned to its source.

In the context of pharmacy data, transactions may include, for example, claim transactions, which relate to an insurance claim by a customer of the pharmacy, and/or inventory transactions, which relate to transfers of product by the pharmacy, including in an over-the-counter context without a corresponding insurance claim.

The accuracy of the information in a claim transaction is vital to ensure that the claim transaction is processed correctly, that the pharmacy is reimbursed accurately, and that PIS data integrity is maintained for every prescription transaction. Unfortunately, due to manual entry that occurs at the pharmacy and errors that may be present in data maintained by the PIS, the claim transaction may not be accurate when processed by the PIS. Furthermore, even when the information in the claim transaction is encoded accurately, the values within the transaction data fields may not be set to process the claim in the optimal manner.

The approaches described here are capable of processing of data records, e.g., transactions, of various formats. Prior to processing of a received transaction, the format of the transaction can be converted into a common format usable by a rules engine. This is sometimes referred to as normalization or translation of the transaction. After the normalized transaction has been processed by the rules engine, the processed transaction can be re-converted into its original format, or into another format, e.g., in accordance with a format specification of a destination for the processed transaction. The normalization of transactions facilitates transaction processing, e.g., by helping to ensure that relevant data fields are located in the transaction and in a standardized location.

The approaches described here enable additional data fields to be created, e.g., in a wrapper associated with a transaction, to contain supplemental data generated during the processing of the transaction. The supplemental data can include, for example, instructions and/or supplementary analyses that are not suitable for storage in the existing data fields of the transaction or its wrapper. The ability to generate supplemental data and to create a data field for the storage of these data allows for flexible and scalable rules engine output.

Systems as described in this disclosure may be used by a PIS to "pre-process" and annotate, as configured, claim transactions prior to sending to other entities, in order to optimize functions such as billing, patient roster management, inventory management, chain of custody, and drug ordering. Additionally, given the increasing complexity of the industry and supporting technology, any entity interacting with the PIS in the "pre-process" capability may benefit from the wrapper included in transactions, the wrapper allowing for more robust instruction sets to be transmitted between the entities.

The technology described herein provides a set of programming interfaces for systems to pass structured data to a configurable rules engine, including, in a pharmacy context, pharmacy-specific analysis rules for assessing and optimizing data. Results are communicated back to the data source (e.g., pharmacy) and/or to third party entities for further processing.

The result of pharmacy data processing by the rules engine, besides providing improvements in data processing and transmission efficiency, can, in some embodiments, improve results in various pharmacy-related areas, including, but not limited to, reimbursement, inventory accuracy, substance tracking, financial management (e.g., accounts receivable (A/R)) accuracy, facility details, and patient demographics of the pharmacy systems. Using a rules engine that is configured with a pre-defined set of rules may allow pharmacies to enjoy a higher level of completeness and accuracy in the information both used for internal processing purposes, as well as any information sent to third parties.

Overview

FIG. 1 provides an overview of a framework for pharmacy data processing. A physician 110 working in a facility 101 (e.g., a hospital or a nursing home) examines a patient 105 and enters a script for a drug into the patient's 105 Electronic Health Record (EHR) 115. The EHR 115 is transmitted electronically or manually to a pharmacy 102 and a claim is processed through various components (described in detail throughout this disclosure) to allow a pharmacist 120 to dispense the requested drug to the patient 105 either directly or via the physician 110.

In the example of FIG. 1, processing at the pharmacy 102 begins when the EHR 115 is read by a pharmacy information system (PIS) 125. A PIS is a software system that assists pharmacists in safely managing the process of dispensing medications. Aside from managing dispensing of drugs, PIS 125 may perform tasks such as, for example, reporting (e.g., utilization reporting or financial reporting); pricing, charging, and billing; and inventory management. The PIS 125 connects to various systems to complete its tasks. In the example of FIG. 1, two such systems are shown: the PIS communications manager (PCM) 130 and the switch provider 140. The PCM 130 is a lightweight software application that integrates with the PIS 125 to enable transactions to be submitted to and received from a pharmacy rules engine 135 (sometimes also referred to as a rules engine). A transaction is a data record having one or more fields containing data related to a prescription. In some embodiments, the functionality of the PCM 130 can be directly integrated into the PIS 125 rather than having a separate software application, as in FIG. 1.

The rules engine 135 is a software application that processes inbound transactions (e.g., claims sent by a pharmacy), checks the inbound transactions against one or more conditions, and can modify the inbound transactions based on pre-configured rules. Depending on the rules governing operation of the rules engine and depending on field values of the transaction itself, the inbound transaction may be modified and/or annotated, for instance by editing values of the fields or by adding supplementary data to a data wrapper of the transaction, and the result is sent back to the PIS 125 for further processing.

For example, for some transactions the supplementary data may include a note to be sent back to the PIS 125 for the pharmacist to review. In some embodiments, the supplementary data includes a command string for the PIS 125 to accept and use to perform an operation within the PIS 125 (e.g., send the claim on for payment, or kick-off workflow X, or add 50 pills of drug Y back to inventory).

The rules engine 135 may be operated, for example, by a Group Purchasing Organization (GPO) such as Managed Health Care Associates Inc.

The switch provider 140 is a computing system configured for receiving, validating, and transmitting claims from the PIS 125 to a pharmacy benefit manager (PBM) 145 that manages the payment for any benefits that may be available to the patient 105. The PBM 145 also handles adjudication of claims. As shown in FIG. 1, the PIS 125 may first interact with the rules engine 135 (resulting in a "modified claim" or recommended actions for the PIS 125 to perform). In some embodiments, the PIS 125 takes a particular response from the rules engine 135 as an indication that it is okay to proceed with its predetermined workflow (e.g., send an unmodified claim to the switch provider 140).

Once a claim is adjudicated by the PBM 145, information related to the adjudication is passed back to the PIS 125 via the switch provider 140 within the claims transaction. As described in further detail throughout this disclosure, one advantage of the integration of the rules engine 135 with the PIS 125 (or, in some embodiments, the communicative connection between the rules engine 135 and the PIS 125) is that claims processing is not limited to any specific format, e.g., not confined to use a standard Electronic Data Interchange (EDI) claim format. For instance, the system can employ a wrapper that can be extended to include data elements and/or instruction sets for the rules engine 135 to leverage, or to facilitate annotation of the transaction that is sent back to the PIS 125. A translation component may be configured to perform any appropriate formatting/reformatting of data elements or transactions to enable the rules engine to process transactions of various formats.

In some embodiments, transactions are transmitted to the rules engine 135 from a third party, such as a third party that provides additional services to the pharmacy 102, e.g., pharmacy data transmission or handling services. Transactions received from third parties can be formatted, processed through the rules engine 135 and transmitted back to the third party and/or the pharmacy 102, e.g., with annotation for further processing. Thus, rather than receiving the initial transaction directly from the pharmacy 102, the rules engine 135 can receive the initial transaction from a third party (e.g., a switch, a payer, or a PBM). The rules engine 135 then processes the transaction and performs one or more specific actions on the transaction.

In some embodiments, the transaction is sent on to a reimbursement platform for consideration in a broader financial management and analytics concern. In some embodiments, the transaction is returned to a third party for additional processing based on additional data elements, as applicable based on rules determination.

Rules Engine

The section that follows provides additional detail regarding the rules engine. Although the examples described below are directed to the processing of pharmacy claims by the rules engine, the rules engine can be utilized for processing a wide array of structured pharmacy data including, but not limited to EHRs, electronic medical records (EMRs), inventory management records, drug chain of custody records, eligibility data, and financial or A/R data. Moreover, the rules engine and its related systems and processes are not restricted to processing pharmacy-related data, but, rather, can be applied to any type of data.

Pharmacies process a wide array of data. The different types of data are relevant to the pharmacy's regular operations, e.g., to ensure that the pharmacy is paid for its services and to allow the pharmacy to provide a high level of care to their patients. The rules engine is capable of addressing the full spectrum of data review, modification, and notification workflows involved with pharmacy data. In some embodiments, an incoming transaction is first translated prior to being provided to the rules engine. Following translation, one or more pharmacy configurable rules are applied to the transaction (sometimes referred to as executing the rules), e.g., to increase the accuracy and completeness of the values in the transaction, such that the transaction can be further processed by the rules engine.

A pharmacy configurable rule is a rule that may be enabled/disabled and/or otherwise modified by the pharmacy sending transaction data or by a larger entity to which the pharmacy belongs. For example, different pharmacies may configure different parameters, e.g., threshold values for comparison of field values in a transactions, or may configure different responses by the rules engine to certain logic results (e.g., a hard rejection of the transaction versus a modification to the transaction). The pharmacy configurable rules may also indicate pharmacy-specific types of supplementary data to be included in returned wrappers.

When processing a transaction, a rules engine extracts values in various fields of the transaction and analyzes them as determined by the pharmacy configurable rules governing the processing of the transaction. For example, the rules engine may compare some values to other values and/or to stored reference data, and, based on the comparison, either reject the transaction or modify the transaction. The rules engine may also add supplementary data to a wrapper of the transaction based on the analysis, e.g., supplementary data indicating that a clinical intervention is necessary, including extending the wrapper to include one or more additional fields. When all pharmacy configurable rules (and, in some embodiments, other analyses) have been performed, the rules engine returns the transaction to a translation component for re-converting to its original data format or to another format.

Figure 2:
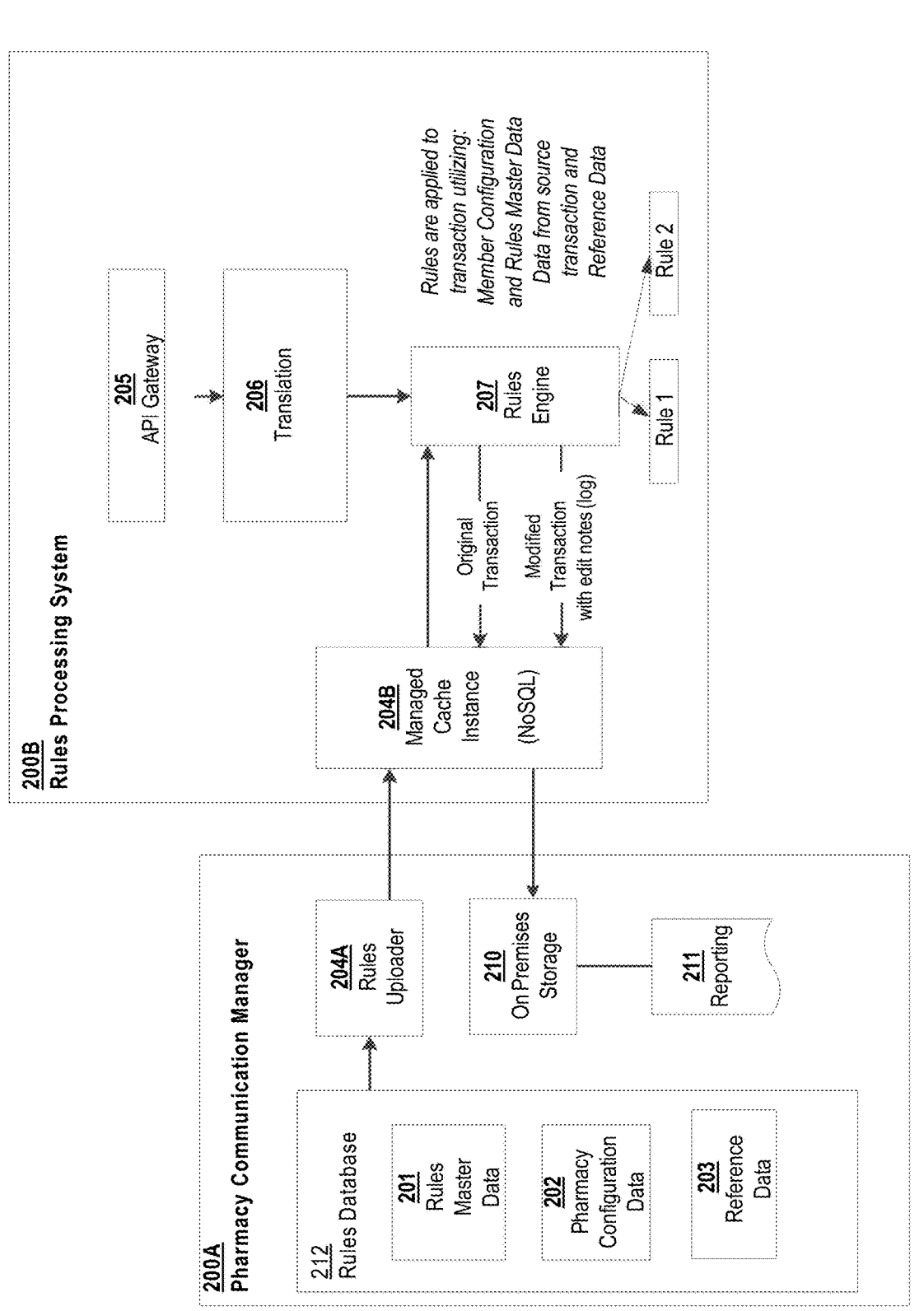
FIG. 2 is a block diagram of an example pharmacy system and an example rules processing system.

FIG. 2 provides a high-level overview of an example system in which the rules engine operates. A PCM 200A at a pharmacy sends transactions to a rules engine 207 in a rules processing system 200B remote from the pharmacy, e.g., a cloud-based rules processing system. These transactions can include information entered by the pharmacist when medication is received or dispensed by the pharmacy, as well as other information about activities, reference data, or configuration data about the pharmacy. The rules engine 207 executes one or more rules to modify and/or annotate the transaction, as appropriate, e.g., by adding one or more fields to the transaction, for further processing by external systems or for internal reporting at the pharmacy. The rules can be implemented individually as micro services running in server-less components within the rules processing system 200B and/or in other computing components of the rules processing system 200B. Once processing is complete, the modified transaction is written and sent back to the PCM 200A.

In the example of FIG. 2, the rules processing system 200B is a remote, cloud-based rules processing system. In some embodiments, a rules processing system is local to a pharmacy system, e.g., the rules engine may process on one or more computers located at a pharmacy (referred to as a non-remote rules engine). Descriptions in this disclosure of embodiments featuring cloud-based systems that include, for example, rules engines, translation components, managed cache instances, and API gateways, may apply also to non-remote rules processing systems. Non-remote rules processing systems may, in various embodiments, provide some or all of the same advantages as described for cloud-based systems, and may receive, transmit, and process data in a similar way as that described for cloud-based systems.

"Cloud computing systems" include at least internet-based processing systems accessible remotely by users. Cloud computing systems may include at least processors, storage devices, and/or memory, in some embodiments virtualized into distinct units operable to perform distinct tasks.

As shown in FIG. 2, the PCM 200A includes a rules database 212, a rules uploader 204a, on-premises storage 210, and a reporting engine 211 for processing transactions. These elements may be, for example, included in the PCM 130 or in the PIS 125 (see FIG. 1).

The rules database 212 holds rules master data 201, pharmacy configuration data 202, and reference data 203. The rules database 212 may be implemented using various database systems. In some embodiments, data is stored in a NoSQL database. The term "NoSQL" is used to define a class of data stores that are non-relational in their design. There are various types of NoSQL databases which may be generally grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of NoSQL database may be used to implement the various embodiments described herein. In some embodiments, relational databases (RDBMS) may be used to implement the rules database 212. Examples of a suitable RDBMS include, without limitation, MySQL, Oracle, SQLite, Postgres and MS-SQL databases. In some embodiments, blockchain is used as a storage medium. For example, in some embodiments, prescriptions are received via a blockchain-based custody model and the rules engine interacts with blockchain to read and update and/or annotate a prescription in a blockchain.

The rules master data 201 includes master data for each of the rules to be processed in the rules engine. The rules master data 201 may include, for example, drug lists, NDCs, States, payor identification data, and/or other data guiding transaction processing. These rules are configurable and may be applied to the transaction by the rules engine 135 prior to responding to the PCM 200A or PIS 125. These rules can, in some instances, be executed to perform an edit to one or more of the fields in the transaction, e.g., to address any issues, e.g., data quality issues. with the transaction. This editing can take place at the rules engine 207. Alternatively, the issues can be reported to the PIS 125 so that the transaction can be managed there. For instance, the rules engine can modify the wrapper to add a field including supplementary data descriptive of the issues, and the editing can take place at the PIS 125 based on the supplementary data in the newly added field of the wrapper.

The rules include at least three broad categories of rules: soft, hard, and cascading. A soft rule, when executed, causes an edit that updates the value in a field of a transaction without manual intervention. A hard rule, when executed, generates supplementary data that flags a transaction for, or triggers, additional processing or interaction at the pharmacy (e.g., by the PIS 125), for example, directing a user to verify the accuracy of a specific field or directly triggering an update to an inventory database of the PIS 125. Finally, a cascading rule, when executed, causes a combination edit that can react as a hard rule or a soft rule based on the values in the transaction fields.

Various types of rules can be executed by the rules engine 207 to process data in various fields of a transaction. Examples of rules can, when executed, cause the pharmacy service type, the medication quantity dispensed, or other data to be checked or altered. Each of one or more of the rules executed by the rules engine 207 can have its own master data that includes one or more of the name of the rule, a rule identification number, and identification of which code contains the logic for the rule (e.g., the name of a specific stored procedure or function). Additional master data for the rule may be stored and identified in the rules master data 201. This additional master data may include, for example, the effective date ranges of each rule or a default rule type that indicates whether a rule will trigger a rejection or an update on-the-fly (e.g., an alteration to the transaction made by the rules engine). The rules can contain configurable options corresponding to one or more rules, and the default settings for the configurable options are stored at in the rules master data 201.

Rules master data 201 may also include pre-requisite rule data. For instance, certain rules are executed after other rules, e.g., because the output of one rule is the input for another rule. In such cases, pre-requisite data can indicate that "Rule X is a pre-requisite for Rule Y." The rules master data 201 can include a rules pre-requisite table storing pre-requisite relationships between rules. Rules that do not have any pre-requisites can be configured to run concurrently with one other or to run sequentially.

In some embodiments, rules are modified over time. When a new version of a rule is created, the previous version of the rule can be stored in the rules database 212 using a version control system. For example, only one version of a rule may be active at a time. When the rule is modified, a new line is created in a master data table, and the expiration date of a preceding version of the rule is set as the start date of the new version minus 1 day.

Processing by the rules engine may make use of reference data. Reference data can include data relating to data format for the transaction and/or wrapper, e.g., mappings between field types and field values, a data format of the incoming transaction, one or more data formats into which the processed transaction is to be converted, or a format for supplementary data added to the data wrapper (e.g., a type of encoded instruction to be included in the wrapper for processing by the PIS). Reference data may also include interface schemas, developer reference materials, standard threshold, and/or settings. Reference data can be different from master data (e.g., National Drug Codes (NDCs) or postal codes) and from customer specific configuration data (e.g., sequencing of rule logic, on/off options for rules, notification options, thresholds, etc.). In some examples, master data, customer specific configuration data, or both may be used in execution of logic rules.

The rules database 212 also stores pharmacy configuration data 202. Pharmacy configuration data 202 include pharmacy-specific data, e.g., data for each pharmacy or associated group of pharmacies. The type of information stored in the pharmacy configuration data 202 may include, for example, a list of which rule(s) and versions of each rule the pharmacy wishes to utilize. For example, the pharmacy configuration data 202 may contain a superset of rules, but pharmacies can specify which rules they wish to have enabled for their pharmacy and which they do not wish to have active. In some embodiments, some or all of the available rules may have configurable options within them. Some or all of these configurable components have default values, and individual pharmacies have the ability to configure the values they wish to use for these configurable components as well.

For example, one item that may be configurable via the pharmacy configuration data 202 is an indicator of whether a particular rule triggers an update to a transaction in real time or a rejection of the transaction. Other configurable items include an indicator of whether a pharmacy wishes to have a particular patient residence code value handled as a rejection or considered to be clean (e.g., not in violation of the rule.) In some embodiments, there are threshold amounts that are configurable in rules. For example, a pharmacy may have the ability to specify that, if a submitted ingredient cost is within a certain percentage of average wholesale price (AWP), an update should be performed on-the-fly. Conversely, if the AWP is greater than the percentage, the update can be rejected. The percentage can be configurable by the user (e.g., by each pharmacy).

In some embodiments, pharmacies have the ability to designate a bank identification number (BIN)/processor control number (PCN) exclusion list via the pharmacy configuration data 202. For example, the pharmacy may identify BIN/PCN combinations that they wish to exclude from running through the rules engine, and the engine will bypass any transactions for this customer when BIN/PCN is equal to a combination on the exclusions list for that customer.

In some embodiments, the rules engine 207 can be purchased and used by an individual pharmacy location. In some embodiments, the rules engine 207 can be purchased and used by a parent company or affiliate entity associated with multiple pharmacy locations in which the rules engine will process transactions for all locations belonging to that parent company or affiliation. The term "purchased" can refer to a complete purchase of the rules engine 207, a licensing of the rules engine 207, or an enrollment in a subscription-based service. If being used at individual location level, the member configurability described above applies for the single location. If used at the parent or affiliate level, the configurations may be applied commonly across all locations of the parent company or affiliate entity, or there can be variation across locations.

In some embodiments, the rules database 212 provides a graphical user interface (GUI) where authorized pharmacies can log on and view/modify their pharmacy configurations. This GUI may be provided, for example, via a web browser accessing a web page hosted by the rules processing system 200B (or a connected service). In some embodiments, the rules uploader 204A or another application within the PCM 200A may provide the GUI.

The rules database 212 also stores reference data 203. This reference data 203 includes any external data to be referenced by the rules engine to execute the rules. Reference data 203 may include, for example, NDC information usable for comparison with the AWP of a drug or other items related to a drug such as package size, package quantity, etc. The reference data 203 may be developed internally or be collected (e.g., licensed) from external third party partners. Other examples of reference data 203 include, without limitation, properties associated with the pharmacies themselves, such as their Class of Trade (COT), or which external services (e.g., provided by the operator of the rules engine 207) they are consumers of and the effective date ranges for those services.

A rules uploader 204A communicates with a managed cache instance 204B in the rules processing system 200B to sync some or all of the data stored in the rules database 212. Synching may be performed, for example, on a nightly basis or as scheduled by the pharmacy. The rules engine 207 then consumes data from the managed cache instance 204B during its operation. The managed cache instance 204B can be a storage medium that is designed to enable fast read and write operations with low latency under high concurrency. Various types of managed caches are known in the art and, in general, any type of managed cache can be employed for interaction with the rules engine 207. In some embodiments, a persistent cache may be used as an alternative, or in addition to, the managed cache instance 204B. Communications between the managed cache instance 204B and the PCM 200A, and other communications between elements of the PCM 200A and elements of the rules processing system 200B, proceed through the API gateway 205 of the rules processing system 200B

Because data is synced from the rules database 212 to the managed cache instance 204B in the rules processing system 200B, the speed of subsequent processing, e.g., by the rules engine 207 and/or by the translation component 206, is improved compared to if data were not synced to the managed cache instance 204B, because the data may be retrieved from the rules processing system 200B itself rather than from the pharmacy remote from the rules engine 207 and the translation component 206.

The managed cache instance 204B can be configured for fast read and write operations with low latency under high concurrency. Syncing the data to the managed cache instance 204B, therefore, may increase the processing speed of data in the rules processing system 200B.

Operation of the rules engine 207 can be initiated by the PCM 200A transmitting a pre-qualified transaction to the rules processing system 200B. The rules processing system 200B implements an application program interface (API) gateway pattern. The API gateway pattern positions an API gateway 205 in front of the rules engine 207. This API gateway 205 then acts as a single point of entry for a defined group of micro services. The API gateway 205 may provide additional functions such as authentication, authorization, traffic management, access control, monitoring, and API version management.

When a transaction is received by the rules processing system 200B, the transaction is trafficked through the API gateway 205. The API gateway 205 performs an authentication process to validate that the sending pharmacy has the appropriate credentials for proceeding through the process. This authentication can be performed, for example, by examining metadata in the packets carrying the transaction. For example, the API gateway 205 may have a local list of IP addresses associated with credentialed pharmacies. The source address field of the packet can be compared to this local list to determine if the sender of the transaction is credentialed. Alternatively, the sender may be prompted to explicitly provide certain information (e.g., a unique identifier) which can be checked by the API gateway 205. Depending on the outcome of this authentication check, the transaction either advances to the rules engine 207 for further processing, or the transaction is rejected. When a rejection occurs, the rules processing system 200B can return an error message to the sender indicating that they are not authorized to access the rules engine 207. If the authorization is authorized, the raw data version of the transaction is stored locally at the rules processing system 200B, as described in further detail below.

The transaction received from the PCM 200A is translated into a format recognizable by the rules engine 207 by a translation component 206. Information in the wrapper of the inbound transaction identifies specific details including, for example and without limitation, which PIS the transaction is from and which version of the PIS was used, etc. During the translation processing, this information may be utilized to fetch some or all of the following information from the managed cache instance 204B: PIS identifier, PIS version, and field mapping used for the values of the transaction (e.g., positions 2 through 7=NABP, positions 8 through 28=NPI). Once this information is fetched and identified, the transaction is then re-formatted into the standard format for the rules engine 207 (e.g., positions 2 through 2=Pharmacy Service Type, positions 3 through 8=BIN). By applying this process, the rules engine 207 may be equipped to handle various layout formats that will be received across various PISs. Because the translated data has a particular structure suitable for analysis by the rules engine 207, it can be referred to as "structured data."

For example, the conversion of an incoming transaction into structured data may include one or more of: reordering values, changing a storage format of values, normalizing or otherwise changing the form of values (e.g., converting from one currency to another or otherwise changing units), adding additional fields holding values that are calculated based on values included in the incoming transaction, indexing values, or removing fields not needed for processing by the rules engine. The structured data therefore may differ from the initial, incoming transaction in both content (the stored values themselves) and in data format (the manner in which the values are held in memory/storage).

Because the field mapping data is stored in the managed cache instance 204B, transaction formatting by the translation component 206 is faster and less network-intensive than if the field mapping data were stored elsewhere, because the translation component 206 fetches the field mapping data directly from the managed cache instance 204B without the field mapping data having to be sent from the pharmacy remote from the managed cache instance 204 and the translation component 206.

The use of the translation component 206 to convert the transaction to a standard format reduces processing errors, e.g., variable type errors. The use of the translation component 206 to convert the transaction prior to processing by the rules engine 207 also increases a speed of processing by the rules engine 207, because the rules engine 207 is able to process the converted transaction with fewer mid-processing format conversions.

Moreover, the use of a structured data format allows the rules engine 207 to perform comparisons, and operations based on, data drawn from different types of incoming transaction. For example, insurance claim transactions and over-the-counter inventory transactions may include the same data fields, but the transactions themselves may be received at the rules processing system 200B in different formats, reducing the efficiency of aggregation and/or comparison of data from both types of transaction. However, once the transactions are converted into a standard structured form, fields (e.g., customer name, drug type, dispensed drug amount) can be directly cross-referenced and processed together with increased efficiency.

After the translation is completed, the translated transaction is advanced to the rules engine 207. The rules engine 207 can be implemented using various computing architectures. For example, the rules engine 207 can be implemented as a highly available and highly scalable solution hosted on the public cloud. High availability can be provided, for example, by using a Platform as a Service (PaaS) component with a high service level agreement with the hosting provider and multi-region deployment to allow seamless failover. High scalability may be provided, for example, with a cloud deployment which allows for either automatic or manual scaling of the rules engine 207 software components.

The process of the rules engine 207 begins with performing certain checks to determine if the transaction is qualified to proceed through the rules. These checks are pre-defined criteria which may disqualify transactions from advancing through the rules. An example of a pre-defined criterion is, "if the transaction is older than 13 months based on date of service compared to transaction date, then do not proceed."

When a transaction fails these preliminary checks, a message may be provided to the PIS indicating that the transaction will not pass through the engine and that the PIS should process the transaction accordingly. In some embodiments, the pharmacy or PIS is provided with a way to "override" the rules engine 207. For example, consider a record that is sent through the rules engine 207 and returned with one or more corrected values. If the pharmacist or PIS opts to not apply the change, they can turn on an override flag in the wrapper data (or some similar identifier) that allows the transaction to go through the rules engine 107 without triggering the same message in subsequent submissions of the transaction.

If the pre-qualifications performed at the API gateway 205 and translation component 206 are passed, the rules engine 207 then acquires the appropriate rules master and member configuration data from the managed cache instance 204B to determine which rules shall be executed for the submitting pharmacy, what the configurable details are for the rules the pharmacy has active (if applicable), and any pre-requisite information to be applied if applicable for the active rules.

Each of the active rules for that pharmacy is executed by the rules engine 207. This entails executing the logic of each rule. Components involved in this process are the data within the transaction, data from the rules master and member configurations records, and reference data which has all been pre-loaded into the managed cache instance 204B as described above.

Once each rule is executed by the rules engine 207, an outcome is rendered for each rule which indicates one or more actions indicated by the PIS. The outcome may indicate, for example, that a rule does not meet criteria for needing change (e.g., that it is "clean"); that the rule is not applicable for some reason (e.g., the NDC cannot be validated); that the rule warrants a rejection of the transaction; or that the rule shall generate an update on-the-fly. There may be a mix of these outcomes across rules; ultimately the outcomes for all of the rules are rolled up into a single outcome that is presented back to the PIS. Additional details around the process of updates in the PIS are detailed below in the section entitled "PIS Updates."

Processing by the rules engine may also operate on the wrapper included with the transaction. The wrapper includes metadata of the transaction (e.g., a source of the transaction and/or a data format of the transaction), but may be distinct from the data values that define the transaction, such as a reimbursement amount and a dispensed drug amount.

The wrapper may have a structure different from the particular data format of the transaction. For example, if a PIS is configured to send and receive a first data format (e.g., a data format usable by switch providers), that first data format defines the structure of the aforementioned data values that define the transaction. By contrast, the wrapper is extensible and modifiable, and may therefore be used by the rules engine to embed supplementary data.

For example, if the rules engine determines that a dispensed drug amount in a transaction requires further review by a pharmacist, there may be no particular data field in the transaction that is configured to hold such an indication. In this case, the rules engine may embed, in the wrapper, a note indicating that the further review is needed.

As another example, for a claim transaction or an inventory transaction, pharmacy-specific logic rules may indicate that a particular result of rules-based processing should result in further processing by the PIS (e.g., a change to inventory values stored by the PIS). However, the rules engine may not be able to directly perform operations within the PIS, and the format of the transaction, excluding the wrapper, as returned to the PIS, does not include a field for indicating the operations.

Therefore, the rules engine may embed, in the wrapper, an encoded instruction indicating to the PIS one or more suggested operations for the PIS to perform. A suitable format for the code instruction may be indicated in the wrapper itself (e.g., as received by the rules processing system from the pharmacy), or may be indicated in a storage of the PCM (e.g., in the pharmacy configuration data 202 or in the reference data 203).

For example, the encoded instruction may include a classification code indicating a type of operation to be performed (e.g., a change in inventory or a message to be sent to a patient), an identifier code (e.g., the particular drug or particular patient), and a parameter field (e.g., an amount by which the inventory is to be changed, or the content of the message to the patient). The configuration of these and other fields/elements of the encoded instruction may be configured by the pharmacy, stored in the PCM 200A, and retrieved by the rules engine (e.g., from a managed cache instance to which the configuration was synched), such that the format of the encoded instruction is compatible with and expected by the PIS. The rules engine configures the format of encoded instruction as configured by the pharmacy. Upon receiving the encoded instructions, the PIS interprets the encoded instruction and carries out the recommended operations. The inclusion of the code instruction allows rules-based processing by the rules engine to directly translate into PIS-side operations without the PIS having to perform its own rules-based processing, reducing the overall burden placed on the PIS.

In some implementations, the encoded instruction includes a scripted command that can be run through an interpreter in the PIS and directly converted into executable code that can be executed by the PIS. The format of the scripted command is configured by the pharmacy for cross-compatibility, as described above.

The wrapper is "extensible" in that additional data fields may be added to the wrapper (e.g., in order to store additional supplementary data). Such modifications to the wrapper do not alter the underlying data or data format of the transaction. Therefore, although the data format of the transaction is re-converted before return of the transaction to the pharmacy, the wrapper may retain its format independent of the re-conversion. This expands the range of the operations and analyses that may be performed by the rules engine, because the rules engine need not confine its output to data that may be directly stored in the transaction in its re-converted form. The transaction itself may also be able to store only a limited total amount of data. By contrast, the wrapper is extensible to store additional data, such that the wrapper allows for increased total supplementary data in addition to more types of supplementary data.

Continuing with reference to FIG. 2, after the rules engine 207 is finished operating, the updated transaction is returned to the translation component 206 for re-conversion back to its original format and/or to another format. The format(s) to which the updated transaction is converted may be indicated in the wrapper of the transaction and/or in a storage of the PCM 200A. For example, in some embodiments, the updated transaction may be converted into both a PIS-specific format and a second format suitable for forwarding to a switch provider.

Updated version(s) of the transaction are stored in the managed cache instance 204B along with, in some embodiments, the original raw version of the transaction. The rules processing system 200B executes a process to sync these original raw data transaction records and modified versions from the managed cache instance 204B to on-premises storage 210 via the API gateway 205.

Reporting and analytics may be performed by a reporting component 211, which may be integrated into the rules engine 207. Reporting capabilities include, for example, reports identifying all transactions, volumes of transactions impacted by the rules engine 207, detailed displays of what precise activity was performed by the rules engine 207, how did pharmacies react and respond to advice from the rules engine 207, and customer value proposition reporting, which projects estimated revenue/profit gained by leveraging the rules engine 207 and estimated revenue/profit "left-on-the-table" by not following advice from the rules engine 207. The reporting component 211 can report an estimated audit risk avoidance dollar amount due to evaluation by the rules engine 207.

The reporting component 211 can be configured to recognize features of transactions that indicate a particular situation or outcome. In an example, the reporting component is configured to recognize indicators of COVID-19 infection in a single transaction or in a group of transactions, as indicated by, for example, types of dispensed drugs. The reporting component 211 may then produce a report indicating a possible COVID-19 outbreak. Because the reporting component 211 can be configured to generate reports based on transactions (e.g., over-the-counter inventory transactions) that are not sent to a switch provider, and because the rules processing system 200B translates transactions into a common, structured format that allows for cross-referencing between different types of transactions, a wider breadth of input data may be analyzed, leading to improved sensitivity to disease outbreaks.

Rules-based processing by the rules engine can include checks for indicators of one or more diseases, and outputs from the rules engine include these indicators. Because the rules engine may process transactions that are not sent to a switch provider, the rules engine is able to perform this processing on a wider breadth of transactions than would be included in, for example, an analysis performed at the switch provider.

In some embodiments, transactions modified by a rules engine are sent from the pharmacy to the switch provider. In some embodiments, some transactions are not subsequently sent to the switch provider. This provides an advantage compared to conventional switch-based transaction analysis systems, because the rules engine and associated components of the rules processing system, by back-and-forth communications allowed by the integration of the PIS and the rules processing system, may evaluate "non-adjudicated" transactions that do not reach the switch provider, e.g., out-of-pocket transactions or Med A transactions. Results of the rules-based processing may then be used to increase received payment amounts, confirm dispensed drug amounts and other transaction fields, and/or modify future pharmacy-side processing (among other possible results of rules-based processing) based on rules engine evaluation of these non-switch transactions.

Pre-processing by the rules engine prior to transaction transmission to the switch provider may decrease overall network transmission volume, because the pre-processing reduces a number of transactions that are rejected at the switch or at the PBM and are then sent back to the pharmacy (e.g., as an adjudicated claim).

Processing by the rules engine can include audit-related evaluations. If a value (e.g., a particular claim amount or a dispensed drug amount in a transaction) satisfies an audit condition (e.g., is likely to lead to an audit of the claim), the rules engine may perform or recommend a modification to the transaction such that the value does not satisfy the condition. For example, the value satisfying the audit condition may be above a threshold amount, and the modification may reduce the value to below the threshold amount, such that the modified value does not satisfy the audit condition. Because of the integration between the PIS and the rules processing system, transaction fields that may lead to an audit may be checked before the transaction is sent to a switch provider. Data indicating various audit conditions (e.g., value thresholds above which an audit is likely) can be stored with other reference data or with pharmacy-specific data.

Processing by the rules engine can include disease prediction. For example, drugs dispensed to a particular patient over time may indicate a particular disease in the patient and/or a change in disease severity. In some embodiments, the rules engine inserts, into the wrapper, supplementary data indicating a need for, or triggering, a clinical evaluation of the patient.

FIG. 3 provides an example of how the rules engine processes. Pre-eligibility, member configuration, and reference data settings are uploaded to the rules engine processing environment (e.g., the managed cache discussed above with reference to FIG. 2) (305). The rules engine iterates through each active rule, utilizing the relevant data in the transaction, applying the logic for the rules while consulting any relevant reference data (310). The activities performed at 310 may include, for example, looking up the class of trade for the submitting pharmacy; looking up the AWP for the NDC in the transaction; looking up various other characteristics of the NDC, e.g., Form type and Package Quantity; and looking up contracted reimbursement rates and dispensing fees. The rules engine renders results for the transaction (315). Examples of these results are shown in Table 1. The results for the transaction are sent back to the PIS for further processing (320).

TABLE 1

| Examples of results rendered by the rules engine. | |
| --- | --- |
| Result | Meaning |
| Not Applicable | None of the active rules qualified to proceed |
| Clean | The transaction met the requirements of each active rule |

TABLE 1-continued

| Examples of results rendered by the rules engine. | |
| --- | --- |
| Result | Meaning |
| Update | "On-the-fly" updates shall be made to the transaction |
| Rejected | Reject the transaction (e.g., at the rules engine or by sending a rejection instruction to the PIS) |

In some embodiments the rules engine receives, from the pharmacy, reversed, previously-adjudicated claims. The rules engine may perform rules-based processing and other functions on reversed transactions, as described for transactions throughout this disclosure.

In some embodiments, the rules engine processes transactions using machine learning techniques. Rules-based processing may evaluate transaction fields using machine learning models, instead of, or in addition to, comparing values to previously-defined thresholds or other particular values. The machine learning model may embody logic rules, including, for example audit conditions, fee evaluations, reimbursement evaluations, and disease prediction.

For example, the rules engine may collect data relating to fees (e.g., Direct and Indirect Remuneration fees) and reimbursement, and use that data to train a machine learning model. The machine learning model may be trained based on data from many pharmacies performing rules-based processing, rather than on data from only one pharmacy or one chain of pharmacies. The machine learning model may also be trained based on other data, e.g., market data. Subsequently, the rules engine, during rules-based processing of a transaction, evaluates fees and reimbursement amounts in the transaction, and, if the fees and reimbursements are inaccurate or unusually high/low, as indicated by the machine learning model, then the rules engine may modify the transaction, reject a transaction, or include an appropriate indicator in processing results. As another example, in some embodiments the rules engine applies a trained machine learning model to predict audit probabilities for transactions.

Although in some embodiments the machine learning model is trained by the rules engine itself or in the rules processing system itself, in some embodiments the machine learning model is created and trained elsewhere and then provided to the rules engine or obtained by the rules engine. Machine learning models may run in the PIS, in the rules processing system, or in both.

In some embodiments, machine learning models, besides being used for the evaluation of individual transactions, are used for multi-transaction or other analyses. For example, in some embodiments, a machine learning model predicts changes in drug copays, and these predictions are relayed to the pharmacy, the rules engine, or both, to inform subsequent decision-making and processing. In some embodiments, a machine learning model, trained based on past transactions evaluated by rules engines, is used to predict future patient demographics and/or drug outflows for one or more pharmacies, such that the pharmacies can manage their inventories more effectively.

In some embodiments, a machine learning model uses real-time data to evaluate pharmacy prices and provide results of the evaluation to pharmacies.

In some embodiments, a machine learning model is used to detect disease outbreaks, as described in more detail above. Inputs to the machine learning model can include transactions associated with multiple patients and multiple pharmacies, including different types of transactions (e.g., both claim transactions and inventory transactions).

Results of the machine learning, besides directly informing modifications to the transaction, may be included in supplementary data added to the wrapper.

Example Configuration and Processing Methods

Figure 4:
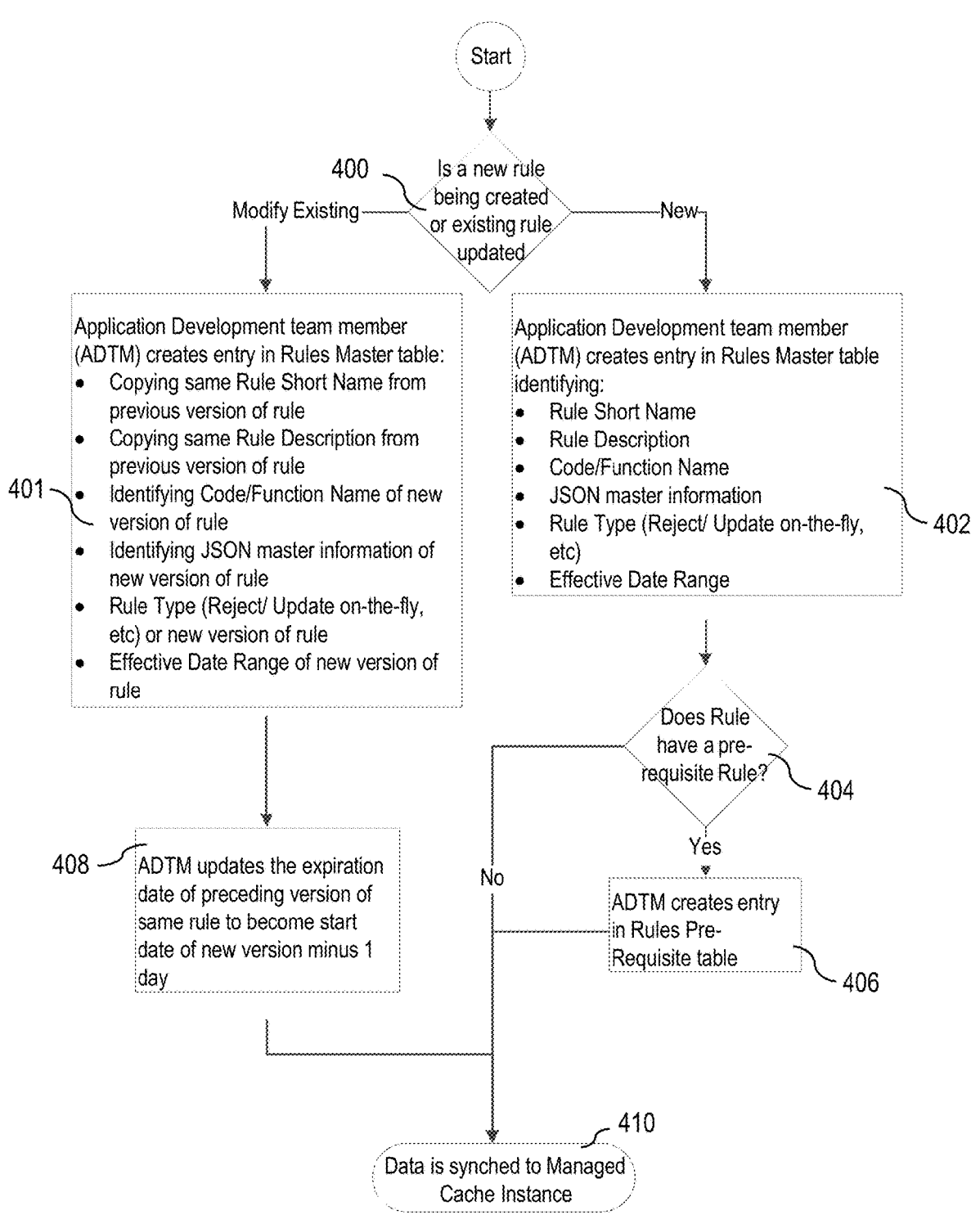

FIG. 4 shows an example of how rules can be added or modified in the rules master table. It is determined whether an entirely new rule is being created or whether an existing rule is being updated to create the new rule (400). If an existing rule is being modified, elements of the existing rule are copied for the new rule (401). If a new rule is being created, those elements are generated (402). The elements may include, for example, a short name of the rule, a description of the rule, a name of a code or function that carries out processing of the rule, data storage information (e.g., JSON master information), a type of the rule (e.g., whether the rule corresponds to a transaction rejection or an on-the-fly alteration of a transaction field), and an effective date range of the rule.

In addition, for a new rule, it is determined whether there is a pre-requisite rule for the new rule (404); if so, an entry indicating the pre-requisite relationship is added to the rules master data (406), e.g., a corresponding entry is added to a rules pre-requisite table.

When an existing rule is being updated, the effective date range of an existing entry corresponding to the rule is modified such that the existing entry expires prior to a start date of the new version of the rule (408). In an example, the existing entry is modified to expire one day before the start date of the new version of the rule.

The new entry in the Rules Master table and any new pre-requisite entry are synced to a managed cache instance (e.g., a cloud-based managed cache instance) with which the rules engine may communicate (410).

Figure 5:
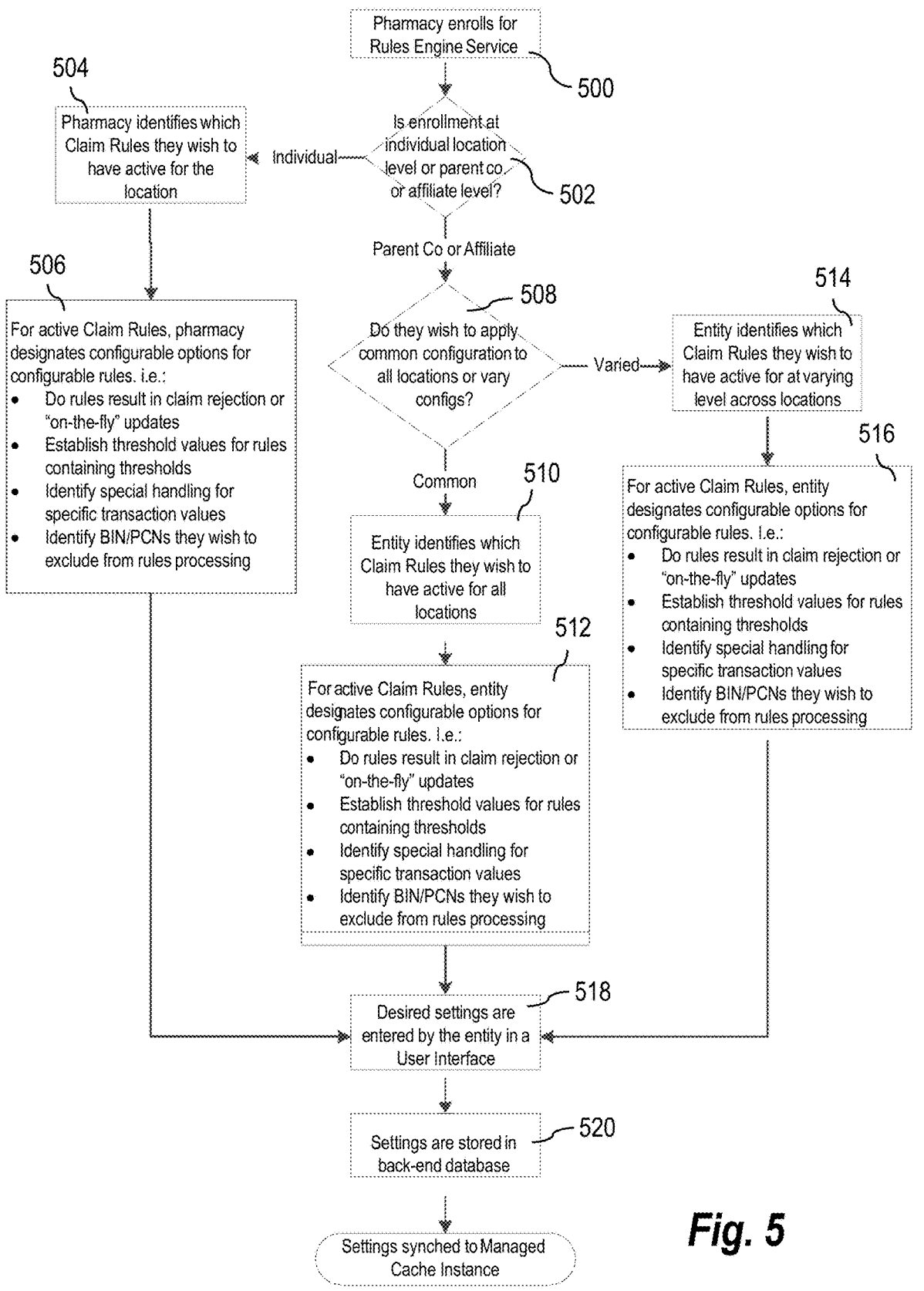

FIG. 5 shows an example of processing of pharmacy configuration data. The processing may be performed by, for example, one or more servers and/or computing devices of a group purchasing organization overseeing a rules engine.

A pharmacy enrolls for rules engine service (e.g., by purchasing a license to use the rules engine service) (500). It is determined whether the enrollment is for an individual location (e.g., one pharmacy) or for a group of locations (e.g., a parent company overseeing multiple pharmacies, or a group of affiliated pharmacies) (502).

For the case of an individual pharmacy, the pharmacy identifies a selection of rules to be applied to transactions sent by the pharmacy (504). For example, a pharmacy may opt to have their drug prices, but not dispensed drug amounts, reviewed by the rules engine.

The pharmacy designates configurable options for any configurable rules selected at 504 (506). For example, the pharmacy may configure results of various rule-based operations, including setting which results lead to rejections compared to on-the-fly alterations and adjusting thresholds for rules.

For the case of a multi-pharmacy company or affiliated group, it is determined whether rules should be common to all locations or whether different locations will have transactions processed by different rules (508). If the rules are to be common, the active common rules are selected (510), and the active rules are configured (512), as described in reference to 504 and 506.

If different rules are to be active for different locations, it is determined which rules are to apply to different locations (514), and those different locations are configured (on a location-wise basis) (516).

The selections of 504 and 506, 510 and 512, or 514 and 516 are entered into a user interface (518).

The entered selections are stored in a back-end database (520), and the stored selections are synchronized to a managed cache instance (522), e.g., a managed cache instance stored in a rules processing system and communicatively linked to a rules engine.

Figure 6:
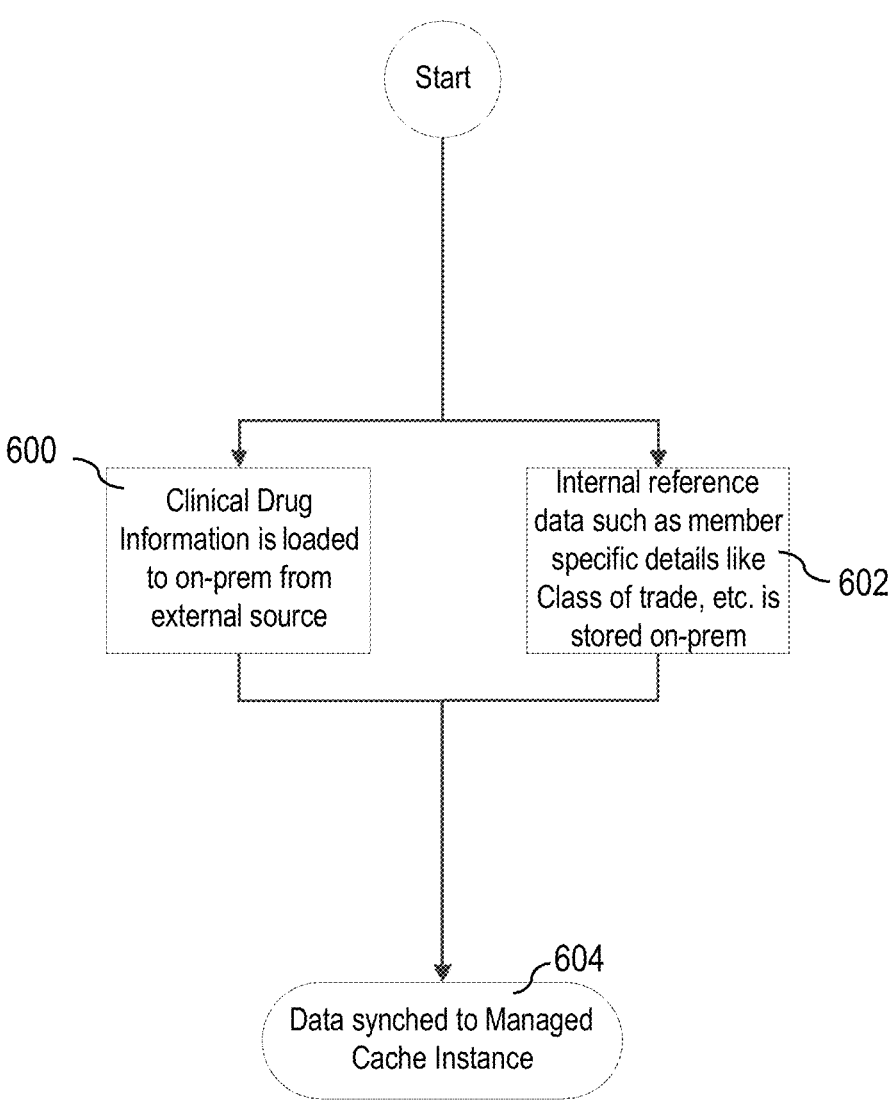

FIG. 6 shows an example of processing of reference data. The processing may be performed by, for example, one or more computing devices of a pharmacy, e.g., a pharmacy communication manager.

Clinical drug information is loaded onto on-premises (local) storage from an external source (600). The clinical drug information can be retrieved from one or more of a drug company database, a government database, or a medical database.

Internal reference data is stored onto the on-premises storage (602). The on-premises storage includes, for example, class of trade data or other details specific to the pharmacy or group of affiliated pharmacies.

The stored on-premises data is synchronized to a managed cache instance (604).

Figure 7:
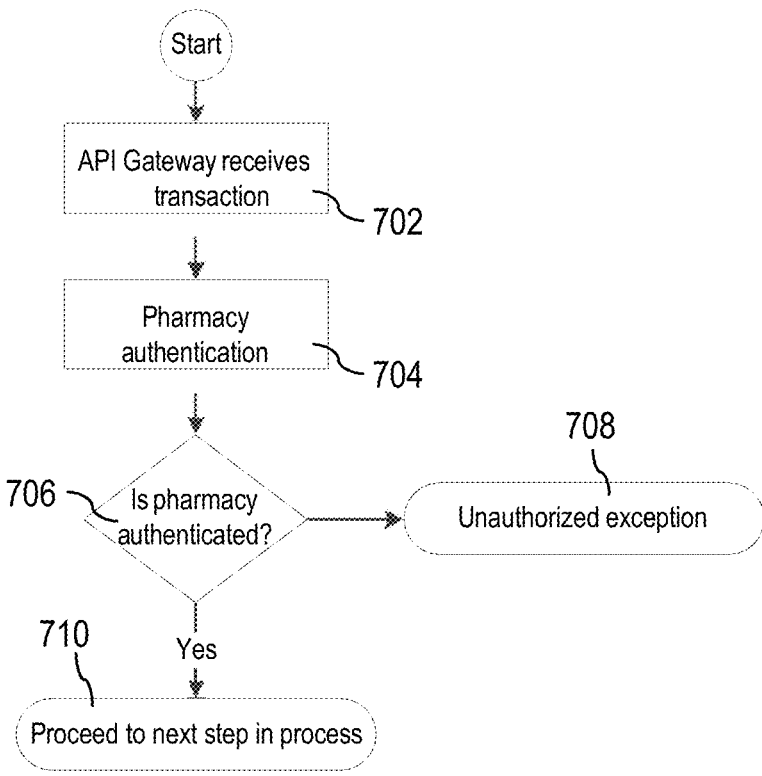

FIG. 7 shows an example of processing by an API gateway. The API gateway received a transaction (702), e.g., a transaction from a pharmacy communication manager or from another source. The transaction can be associated with a transaction, e.g., a request for drug dispensing.

The source of the transaction (e.g., the pharmacy) is authenticated (704).

It is determined whether the pharmacy or other transaction sender is authenticated (706). If the pharmacy or other sender is not authenticated, the transaction is rejected (708). In some embodiments, a notification of an unauthorized exception (rejection of the transaction due to lack of authorization) is returned to the sender of the transaction.

If the pharmacy or other sender is authenticated, processing (e.g., by a rules processing system) proceeds (710), e.g., proceeds to translation.

Figure 8:
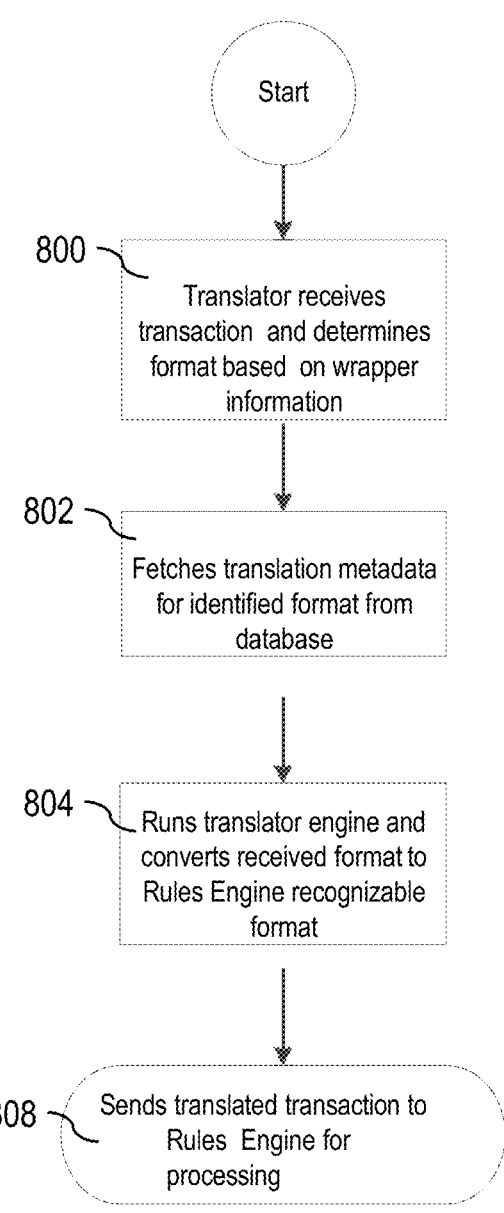

FIG. 8 shows example of how processing by a translator is performed. A translator receives a transaction and determines data format and other data information (e.g., information about a PIS that sent the transaction) based on information included in a wrapper of the transaction (800). In some embodiments, data included in the wrapper is cross-referenced to configuration data stored in a PCM in order to determine the data format.

The translator fetches translation metadata (e.g., field mappings and/or data units) associated with the determined data format, for instance from a managed cache instance or from the PCM (802).

The translator converts data in the transaction into a format recognizable by a rules engine communicatively linked to the translator (804). As described above, this conversion may include not just reordering/reconfiguring of existing fields, but also the addition of new data fields and/or the conversion of existing values into a different form.

The translated transaction is sent to the rules engine for rules-based processing (806).

Figure 9:
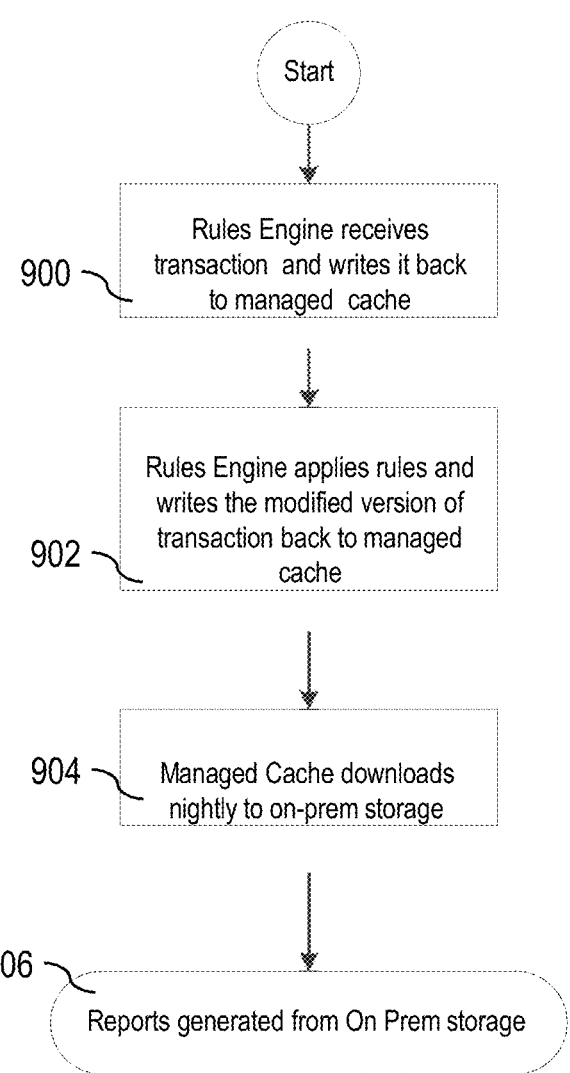

FIG. 9 provides an example of how transaction reporting may be performed by a rules engine and a managed cache instance. The rules engine receives a transaction and writes the transaction to the managed cache instance (900). The rules engine applies active rules (902), which can result in modification of a transaction included in the transaction and/or the generation of supplemental data that is added to a wrapper of the transaction. The rules engine may modify a data format of the wrapper (e.g., add additional fields to the wrapper) in order to accommodate the generated supplemental data. The rules engine then writes the modified version of the transaction (including the wrapper) to the managed cache instance.

The managed cache instance synchronizes data with on-premises storage of a pharmacy (904) via an API gateway. The synchronization can be real-time or near-real-time or can follow a predetermined schedule, e.g., a nightly schedule.

Based on data in the on-premises storage, a reporting component (e.g., a reporting component of a pharmacy communication manager) generates a report (906). The report may indicate, for example, differences between the original transaction in the transaction and the modified version of the transaction. In some embodiments, the reporting component is integrated into rules processing system, e.g., into the rules engine. In some embodiments, the report is stored in the wrapper.

Examples of Claims Rules

The sections that follow detail examples of rules for updating pharmacy claims data prior to submission to payers. Processing according to these example rules includes determining values within pharmacy claim transactions, comparing the values to a mixture of publicly available and proprietary data elements, and updating transactions based on the logic within the rule. The rules are designed such that they may aid in optimizing reimbursement while causing relatively little disruption to pharmacy workflows. Three example rules types are described below: a pharmacy service type claim rule, a contract rate validation claim rule, and an AWP claim rule. In some embodiments, each of these and other rules described in this disclosure may be implemented as several rules, e.g., a given rule may include several checks and/or operations, or the several checks and/or operations may each be included in a distinct rule.

Pharmacy Service Type Claim Rules

Pharmacy claims are often rejected, forcing the pharmacy to manually update and resubmit a corrected claim. As the claim volume for a pharmacy grows, this leads to more personnel time spent updating claims. Being able to automatically update claims for adjudication without the need for manual intervention improves the speed of submission to the payers as well as decreasing employee time spent updating claims that have already been submitted. Additionally, applying claims rules through a direct integration with pharmacy systems, including leveraging extensible wrappers that allow for instructions to be provided by rules processing systems to pharmacy systems, allows for a robust interaction set that helps the pharmacy systems have accurate representations of transactions as well as maintain accurate related information such as inventory, accounts receivable, and other pharmacy-side information.

Some rule yields an action of "update on-the-fly" to a claim when the rule determines the pharmacy service type code value of the claim is not equal to a predetermined value. This updating may help the pharmacy attain an increased reimbursement, e.g., the maximum expected reimbursement. The benefit of having a claim rule enforce an "update on-the-fly" action is that pharmacy work-flow is not disrupted due to this rule, such that rules-based processing using the pharmacy service type claim rule supports efficient operations at the pharmacy while concurrently delivering the benefits of increased reimbursement based on the modifications made by the rules engine In some embodiments, processing for the pharmacy service type rule begins with identifying the pharmacy by the National Provider Identifier (NPI) or National Council for Prescription Drug Programs (NCPDP) value within each transaction. Reference data available in the rules engine processing environment (e.g., in a managed cache instance) is then consulted to determine the class of trade for the submitting pharmacy.

For example, a claim can be received from a long-term care pharmacy. If the class of trade field in the transaction data is set to a value other than, for example, "Long Term Care (LTC)/Nursing Home Provider," the transaction is not eligible for proceeding with the rule. For LTC pharmacies, a pharmacy service type code value that was received in the transaction is evaluated. The pharmacy service type code of LTC pharmacies is "05." Thus, if the pharmacy service type code value is equal to '5' or '05' (depending on how many position values the PIS provides, based, for example, on metadata identified by a translator), then the result of this rule is deemed to be "clean," meaning no updates are necessary in accordance with the rule. If the value is other than "5" or "05" for an LTC pharmacy, then the rules engine recommends an update on-the-fly in the claims whereby the PIS shall automatically replace the original value with "05" and then proceed to process the transaction. In some embodiments, the rules engine automatically performs this on-the-fly update and sends the modified claim back to the PIS.

In some embodiments, for the pharmacy service type claim rule, the rules-based system has reference data that identifies the class of trade for each pharmacy submitting a claim. Thus, the rules engine, when processing according to this claim rule, has the ability to consult and consume the reference data at processing run-time, and, as a result, the rules-based system may provide updates made on-the-fly rather than rejecting claims and causing disruptions to the pharmacies' work-flow. In addition, the rules-based system, by performing or recommending the updates to pharmacy service type values, increases reimbursement amounts received by the pharmacies.

Contract Rate Validation Claim Rule

Some rules are configured based on pharmacies' individual contractual agreements with payers. Having a rule set that addresses the specific rules outlined in a pharmacy's contract increases expected reimbursement.

Like pharmacy service type rules, in some embodiments, a contract rate validation rule includes certain checks. The checks for contract rate validation rules may include, for example, checking for contract terms which exclude compounds and checking whether the prescription is for a compound; if the contract terms exclude compounds and the prescription is for a compound, the rule will not proceed. Three other example checks are: whether the NDC is found within the items reference data, whether the submitting pharmacy has contract specific data, and whether the BIN/PCN combination is a combination for which the contract has specific reimbursement rates. In some embodiments, if any of the latter three checks return a negative response, processing according to the rule does not proceed.

In some embodiments, an ingredient cost submitted value in the transaction (claim) is queried against an AWP (per unit) from reference data. If the ingredient cost submitted value is lower than the AWP amount and the rules engine is configured to update claims on-the-fly, the rules engine modifies the ingredient cost submitted to the AWP amount. Alternatively, if on-the-fly updates are not enabled, the rules engine can advise the PIS to reject the claim when the ingredient cost submitted value is lower than the AWP.

"Advice" to the PIS may not be a direct modification to the value in question or a direct rejection of the claim. Rather, in some embodiments the rules engine advises the PIS by including an appropriate statement in the wrapper when returning the transaction to the PIS. The statement may be an encoded instruction interpretable by the PIS to recommend and/or indicate the modification or rejection, or may be a scripted command interpretable by the PIS to produce executable code that, when executed by the PIS, causes the value to be updated or the claim rejected.

In some embodiments, the contract rate validation claim rule also queries a dispensing fee submitted amount in the transaction and reconciles the dispensing fee against minimum dispensing fee amounts in accordance with the terms of negotiated contracts. Checks associated with the dispensing fee may result in the rules engine advising the PIS to increase the dispensing fee to the contracted amount if the received dispensing fee in the transaction is lower than the contracted amount. Depending on the embodiment and how the pharmacy has configured the rule, the rules engine may perform an update on-the-fly or give advice to PIS to reject the claim.

After ingredient cost submitted and dispensing fee submitted have been checked, in some embodiments the rules engine checks a gross amount submitted in the transaction. Here, the check is to confirm that the gross amount due is equal to or greater than the sum of [adjusted] ingredient cost submitted+[adjusted] dispensing fee submitted. If the gross amount is lower, the rules engine may advise the PIS to increase the gross amount due to the calculated value, e.g., the rules engine may perform an update on-the-fly, or the rules engine may advise the PIS to perform the update, or the rules engine may advise claim rejection in accordance with the pharmacy's configuration.

In some embodiments, the usual and customary value field in the transaction data can be checked as part of the contract rate validation rule or as part of another rule. The rule for this field may vary depending on whether the drug is a branded drug or a generic. For example, some insurance plans have negotiated contracted reimbursement rates for some generics, while and not for other generics. These pharmacy-specific and/or insurance plan-specific negotiated values can be retrieved by the rules engine from the managed cache instance or PCM.

In some embodiments, for drugs with negotiated contracted reimbursement rates, the rules engine checks to verify whether the usual and customary value is equal to or greater than the sum of (AWP−the contracted percentage of transaction fees)+[adjusted] dispensing fee submitted value. For drugs and plans that do not have negotiated contracted reimbursement rates, the check is to verify whether the usual and customary value is equal to or greater than [adjusted] dispensing fee submitted. In either case, the rules engine either updates the usual and customary value on-the-fly and increase the usual and customary value to the calculated amount if the usual and customary value was lower (or advises such a change to the PIS), or advise a rejection if the usual and customary value was lower and the rule is configured to generate a rejection.

Values in the submitted claims are compared to the dispensing fee submitted and usual and customary values, which are unique rates specific for each plan in accordance with negotiated/contracted rates with the pharmacy service provider. Having the ability to make these precise, pharmacy-specific comparisons allows for higher and more reliable reimbursement, compared to systems that compare to only flat/standard or more ambiguous rates. In addition, the fact that the contract rate validation rule assesses and potentially modifies/augments two additional fields (gross amount due and usual and customary value) beyond the industrial standard two fields (ingredient cost submitted and dispensing fee submitted) is beneficial to pharmacies, as also checking these values may generate greater opportunity for increased reimbursement.

In some embodiments, the contract rate validation rule triggers an "update on-the-fly" action resulting in delivering improved reimbursement opportunities without disrupting work-flow within the pharmacy. In some embodiments, the rule is configured to result in a rejection, if the pharmacy or group of pharmacies so chooses to make such an election.

Because the rules engine performs a comparison between the dispensing fee submitted amount in a claim and any proprietary rates that have been negotiated and contracted with the pharmacies (e.g., based on data included in a managed cache instance and received from the pharmacy), reimbursement amounts may be increased. This provides an advantage over systems that perform comparisons against a standard/blanket rate, e.g., because these products do not store pharmacy- and/or contract-specific data. Additionally, the contract rate validation rule checks gross amount due and usual and customary values in submitted claims, whereas other systems may assess only ingredient cost submitted and dispensing fee submitted.

Figure 10:
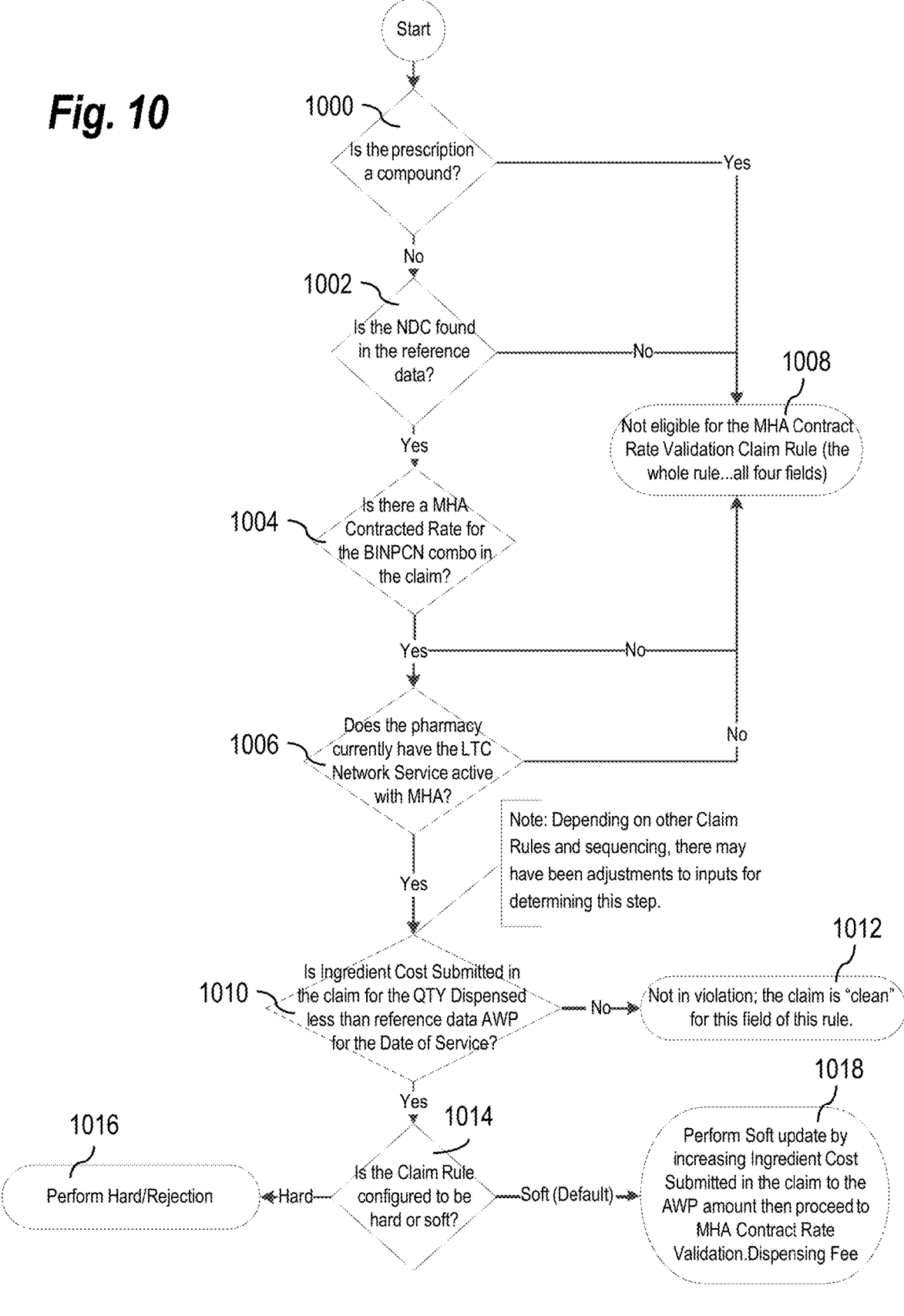

FIG. 10 provides an example of processing, by a rules engine, associated with a contract rate validation claim rule. The rules engine determines whether the drug in a received transaction is a compound (1000). The rules engine determines whether NDC data for the drug is included in reference data accessible to the rules engine (1002). The rules engine checks whether a BIN/PCN combination in the claim corresponds to a contracted rate of a group purchasing organization (GPO) (e.g., Managed Healthcare Associates (MHA) (1004)). The rules engine checks whether the pharmacy sending the transaction has a long term care (LTC) service active with the GPO (1006).

If the result of 1002, 1004, or 1006 is negative, or if the result of 1000 is positive, the rules engine determines that the transaction is not eligible for further processing according to the contract rate validation claim rule (1008).

Otherwise, the rules engine determines whether an ingredient cost submitted in the transaction (for the dispensed drug quantity) is less than a corresponding AWP amount as found in reference data accessed by the rules engine (1010). The checked ingredient cost submitted can be a modified ingredient cost submitted (e.g., modified on-the-fly in processing according to another rule or the same rule).

If the answer at 1010 is negative, the rules engines determines that the ingredient cost field is "clean," and may proceed to other rules-based processing (1012). Otherwise, the rules engine determines (based on, for example, a pharmacy-specific rule configuration) a result of the rule-based processing (1014). In some embodiments, the rules engine rejects the transaction and ceases transaction processing (1016); in some embodiments, the rules engine increases ("on-the-fly") the ingredient cost value to the corresponding AWP amount and continues to perform other rules-based processing (1018).

FIG. 11 provides an example of processing, by the rules engine, associated with a contract rate validation claim rule. The rules engine checks whether a (possibly already modified on-the-fly) dispensing fee value in the transaction is less than a reference dispensing fee corresponding to the drug in the transaction (1100), the reference dispensing fee being determined from a reference storage (e.g., a managed cache instance).

If the result at 1100 is negative, the rules engines determines that the dispensing fee field is "clean," and may proceed to other rules-based processing (1102). Otherwise, the rules engine determines (based on, for example, a pharmacy-specific rule configuration) a result of the rule-based processing (1104). In some embodiments, the rules engine rejects the transaction and ceases transaction processing (1106); in some embodiments, the rules engine updates ("on-the-fly") the dispensing fee value to the reference dispensing fee and continues to perform other rules-based processing (1108).

Figure 12:
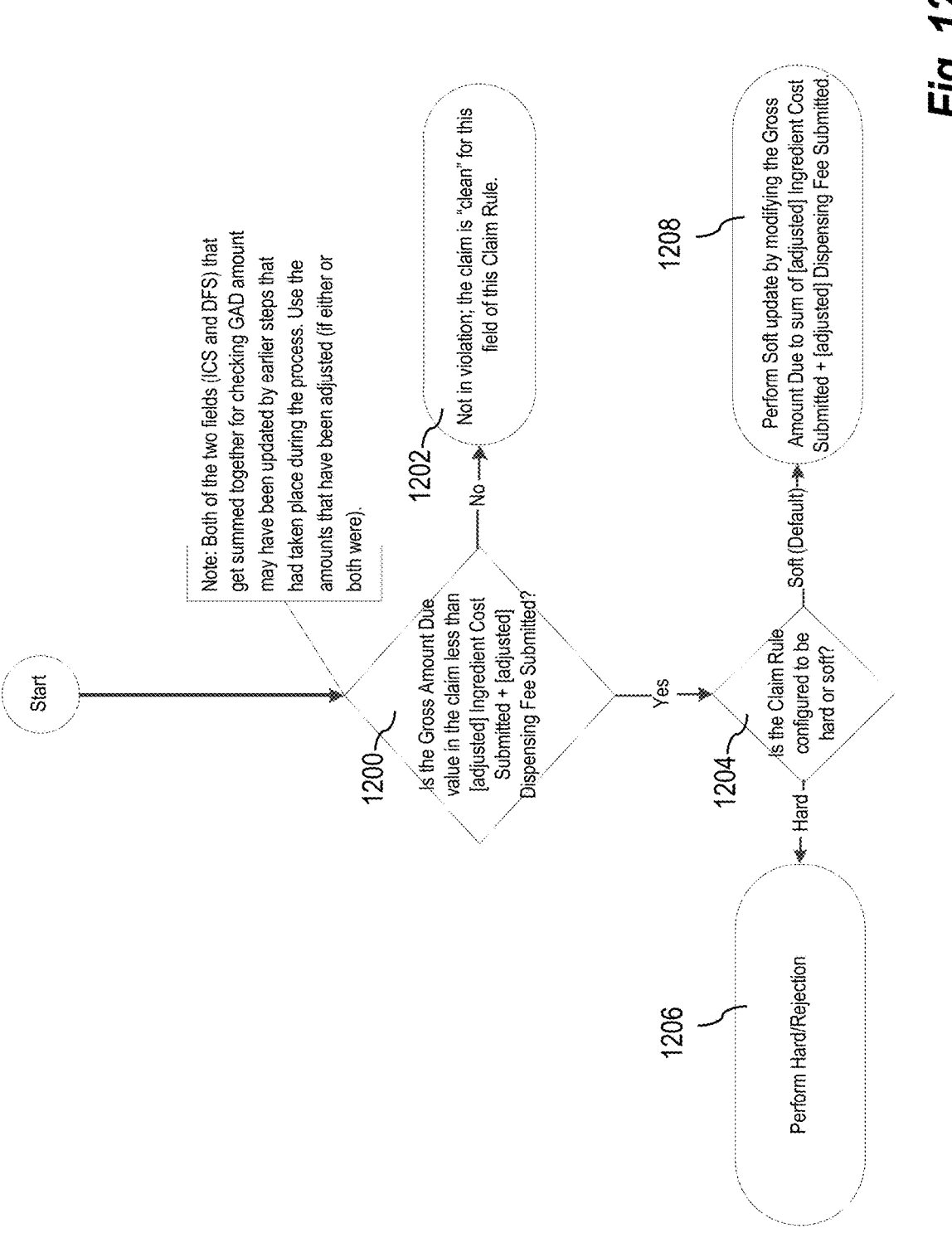

FIG. 12 provides an example of processing, by the rules engine, associated with a contract rate validation rule. The rules engine checks whether gross amount due value in the transaction is less than a sum of an ingredient cost value in the transaction and a dispensing fee value in the transaction (1200). Any or all of these values may have already been modified according to previous rules-based processing.

If the result at 1200 is negative, the rules engines determines that the gross amount due field is "clean," and may proceed to other rules-based processing (1202). Otherwise, the rules engine determines (based on, for example, a pharmacy-specific rule configuration) a result of the rule-based processing (1204). In some embodiments, the rules engine rejects the transaction and ceases transaction processing (1206); in some embodiments, the rules engine updates ("on-the-fly") the gross amount due value to the sum of the ingredient cost value and the dispensing fee value, and may proceed with other rules-based processing (1208).

Figure 13:
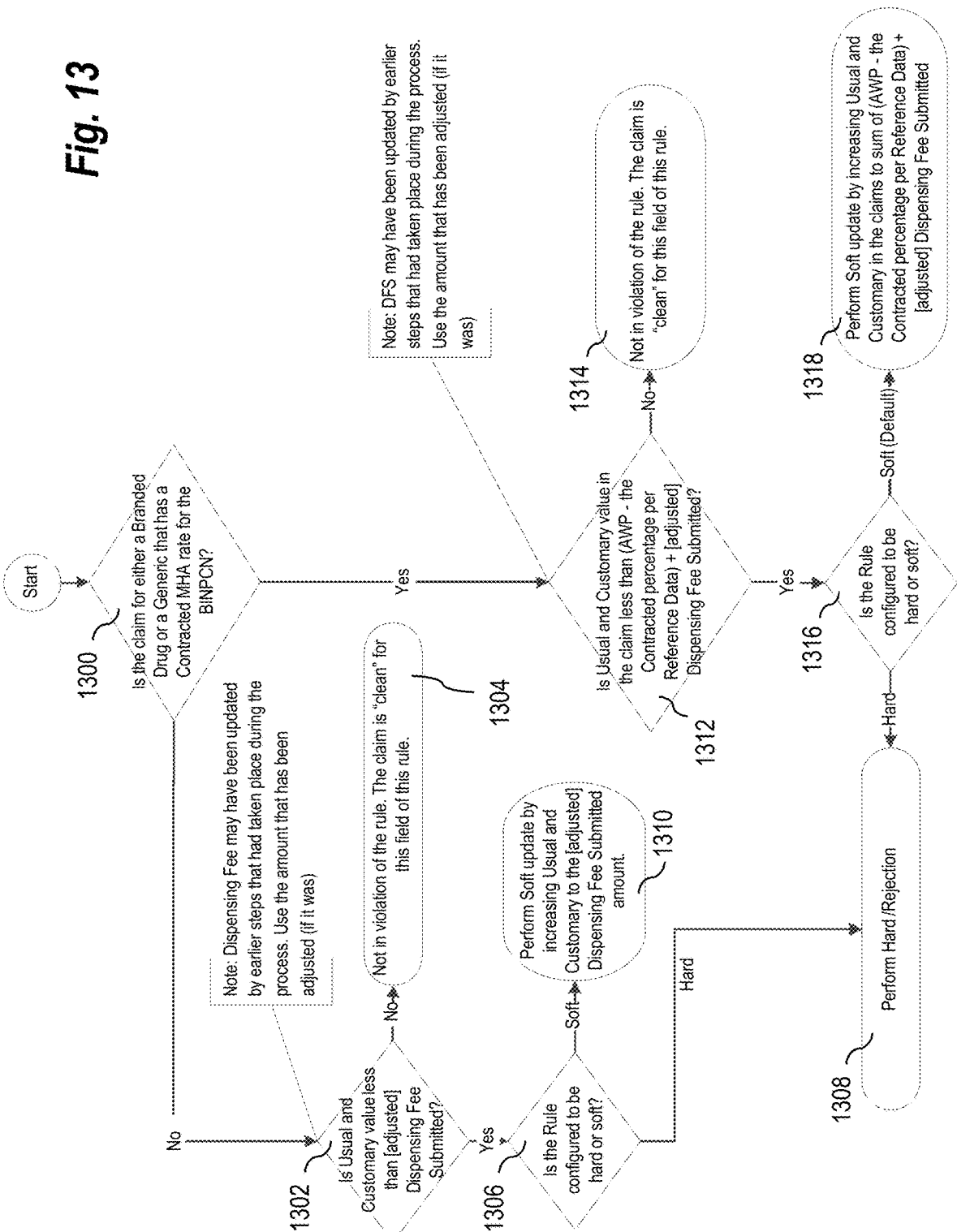

FIG. 13 provides an example of processing, by the rules engine, associated with a contract rate validation rule. The rules engine determines whether the transaction is for either a branded drug or for a generic that has a contracted GPO rate for the BIN/PCN combination of the transaction (1300).

If the result of 1300 is negative, the rules engine determines whether a usual and customary value in the transaction, corresponding to the branded drug or generic, is less than a dispensing fee included in the transaction, which may have been previously adjusted (1302).

If the result at 1302 is negative, the rules engines determines that the usual and customary value field is "clean," and may proceed to other rules-based processing (1304). Otherwise, the rules engine determines (based on, for example, a pharmacy-specific rule configuration) a result of the rule-based processing (1306). In some embodiments, the rules engine rejects the transaction and ceases transaction processing (1308); in other embodiments, the rules engine updates ("on-the-fly") the usual and customary value to the dispensing fee, and may proceed with other rules-based processing (1310).

If the result of 1300 is positive, the rules engine determines whether the usual and customary value in the transaction is less than (AWP–contracted percentage)+dispensing fee (1312), where some or all of these values may be determined by consulting reference data.

If the result at 1312 is negative, the rules engines determines that the usual and customary value field is "clean," and may proceed to other rules-based processing (1314). Otherwise, the rules engine determines (based on, for example, a pharmacy-specific rule configuration) a result of the rule-based processing (1316). In some embodiments, the rules engine rejects the transaction and ceases transaction processing (13108); in some embodiments, the rules engine updates ("on-the-fly") the usual and customary value to (AWP–contracted percentage)+dispensing fee), and may proceed with other rules-based processing (1318).

In some embodiments, the rules engine performs field evaluation based on values already adjusted on-the-fly by the rules engine. For example, a rule may indicate that a transaction is to be rejected if the usual and customary value is lower than a newly-calculated gross amount due. Payers sometimes specify within their rates that they will pay the lowest of the usual and customary value, the gross amount due, and the ingredient cost submitted, but payers are sometimes sent pricings based on differently-calculated versions of these fields, causing underbilling. In some embodiments, the rules engine rejects the transaction if the usual and customary value is lower than the gross amount due or the ingredient cost submitted, including based on newly-calculated values of the gross amount due or the ingredient cost submitted, such that pricing follows adjustments made the rules engine and reimbursement is increased.

AWP Claim Rule

Failing to analyze a gross amount due (GAD) can lead to under-reimbursement when payers look at the GAD for reimbursement purposes.

In some embodiments of the present disclosure, an AWP claim rule is implemented as a subset of a contract rate validation rule. However, the AWP claim rule may also be available to any pharmacy, regardless of the availability of the pharmacy's negotiated contract reimbursement rates. This rule may apply the same checks as the contract rate validation rule for checking compound and NDC validation, but may not have checks for checking BIN/PCN combination or a check for the availability of contract rate data. The AWP claim rule and other rules may apply updates for ingredient cost submitted and gross amount due even for claims without BIN (such as paper-billed transactions).

Figure 14:
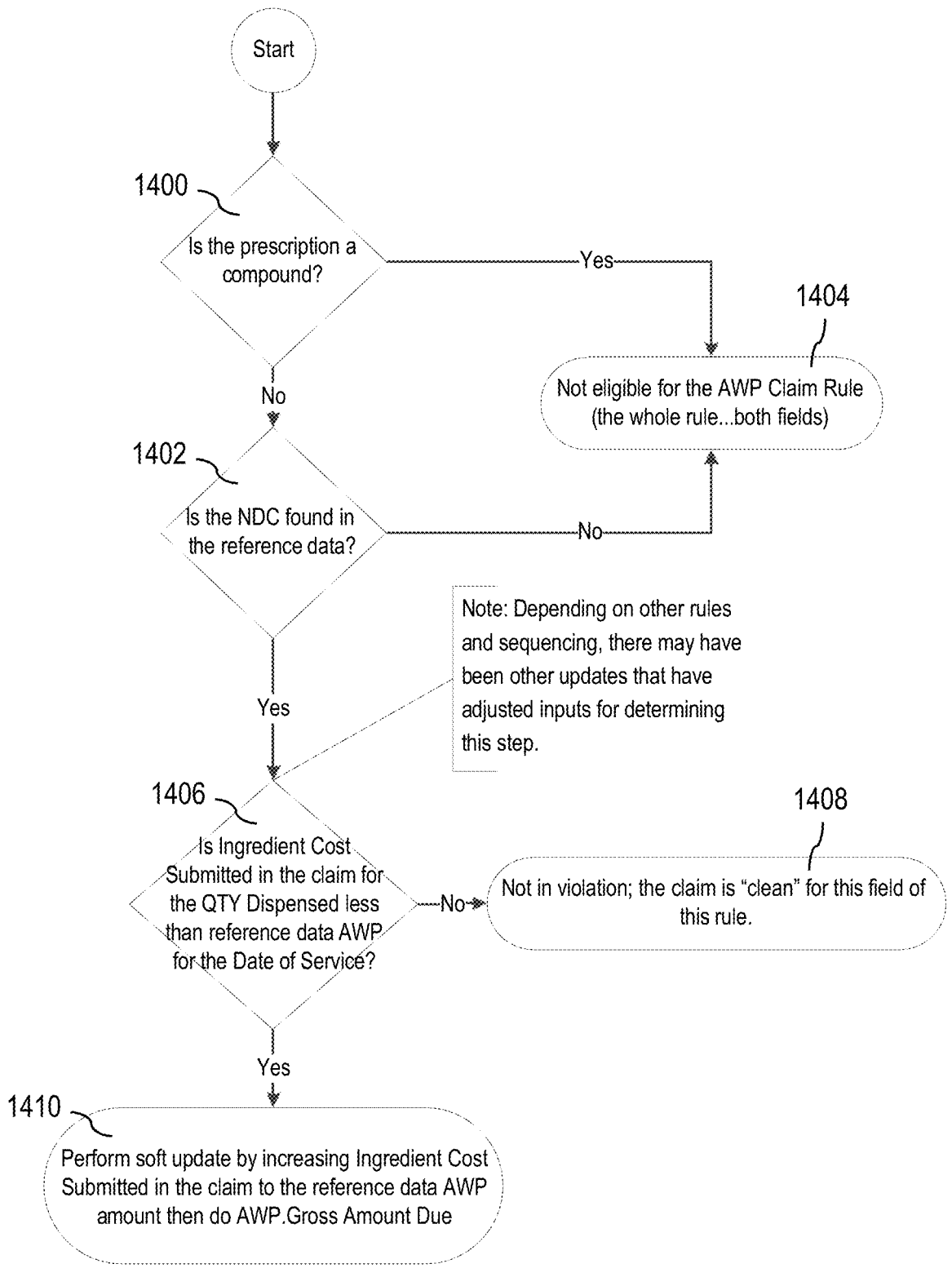

FIG. 14 provides an example of processing, by the rules engine, associated with an AWP claim rule. Ingredient cost submitted is checked in this rule and advised for update on-the-fly in accordance with similar logic as described above in reference to a checked ingredient cost in the contract rate validation rule.

The rules engine determines whether the drug in a received transaction is a compound (1400). The rules engine determines whether NDC data for the drug is included in reference data accessible to the rules engine (1402).

If the result of 1400 is positive and/or the result of 1402 is negative, the rules engine determines that the transaction is not eligible for further processing according to the AWP claim rule (1404).

Otherwise, the rules engine determines whether an ingredient cost submitted in the transaction (for the dispensed drug quantity) is less than a corresponding AWP amount, for the date of service, as found in reference data accessed by the rules engine (1406). The checked ingredient cost submitted can be a modified ingredient cost submitted (e.g., modified on-the-fly in processing according to another rule or the same rule).

If the answer at 1406 is negative, the rules engines determines that the ingredient cost field is "clean," and may proceed to other rules-based processing (1408). Otherwise, the rules engine increases ("on-the-fly") the ingredient cost value to the corresponding AWP amount and continues to perform other rules-based processing (e.g., to check a gross amount due) (1410).

For checking gross amount due in an AWP claim rule, similar logic is performed as described in reference to FIG. 12 (a contract rate validation rule), except that, for the AWP claim rule, there may be no chance for the dispensing fee submitted to have been already advised for update or updated, so only the dispensing fee submitted amount that was directly submitted in a transaction may be factored in.

Figure 15:
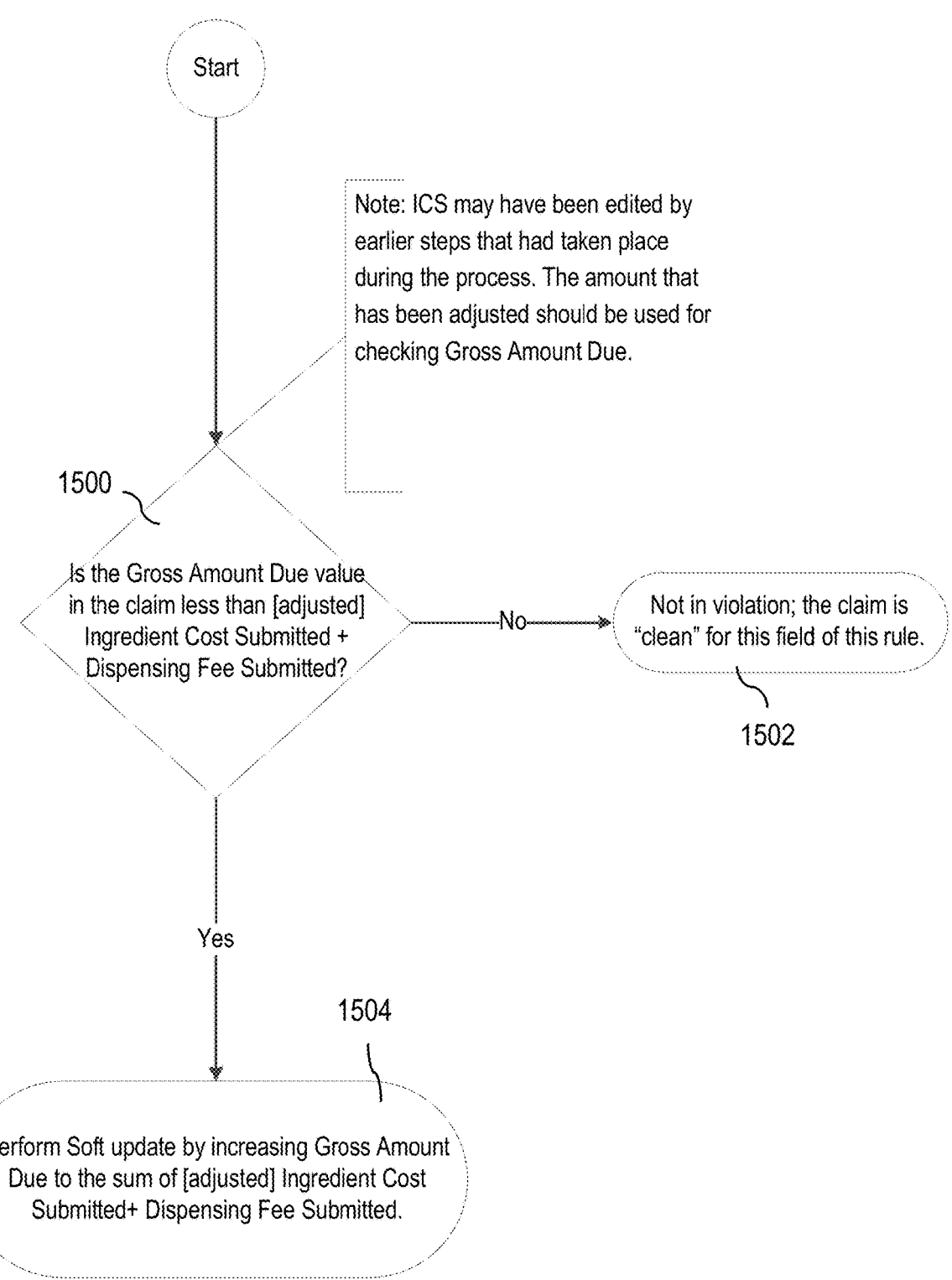

For example, FIG. 15 shows an example of processing, by a rules engine, associated with an AWP claim rule. The rules engine determines whether a gross amount due is less than a sum of the ingredient cost and the dispensing fee, where the ingredient cost has been updated by previous rules-based processing (1500).

If the answer at 1500 is negative, the rules engines determines that the gross amount due field is "clean," and may proceed to other rules-based processing (1502). Otherwise, the rules engine increases ("on-the-fly") the ingredient cost value to match the sum of the ingredient cost and the dispensing fee and continues to perform other rules-based processing (e.g., to check a gross amount due) (1504).

One benefit of AWP claim rules, as described in this disclosure, is that the rules not only check and potentially modify ingredient cost submitted, but also check and potentially modify gross amount due. By having this additional field in-play for checks and modifications, processing according to the rules benefits pharmacies by generating greater opportunity for increased reimbursement.

Pharmacy Service Type

Figure 16A:
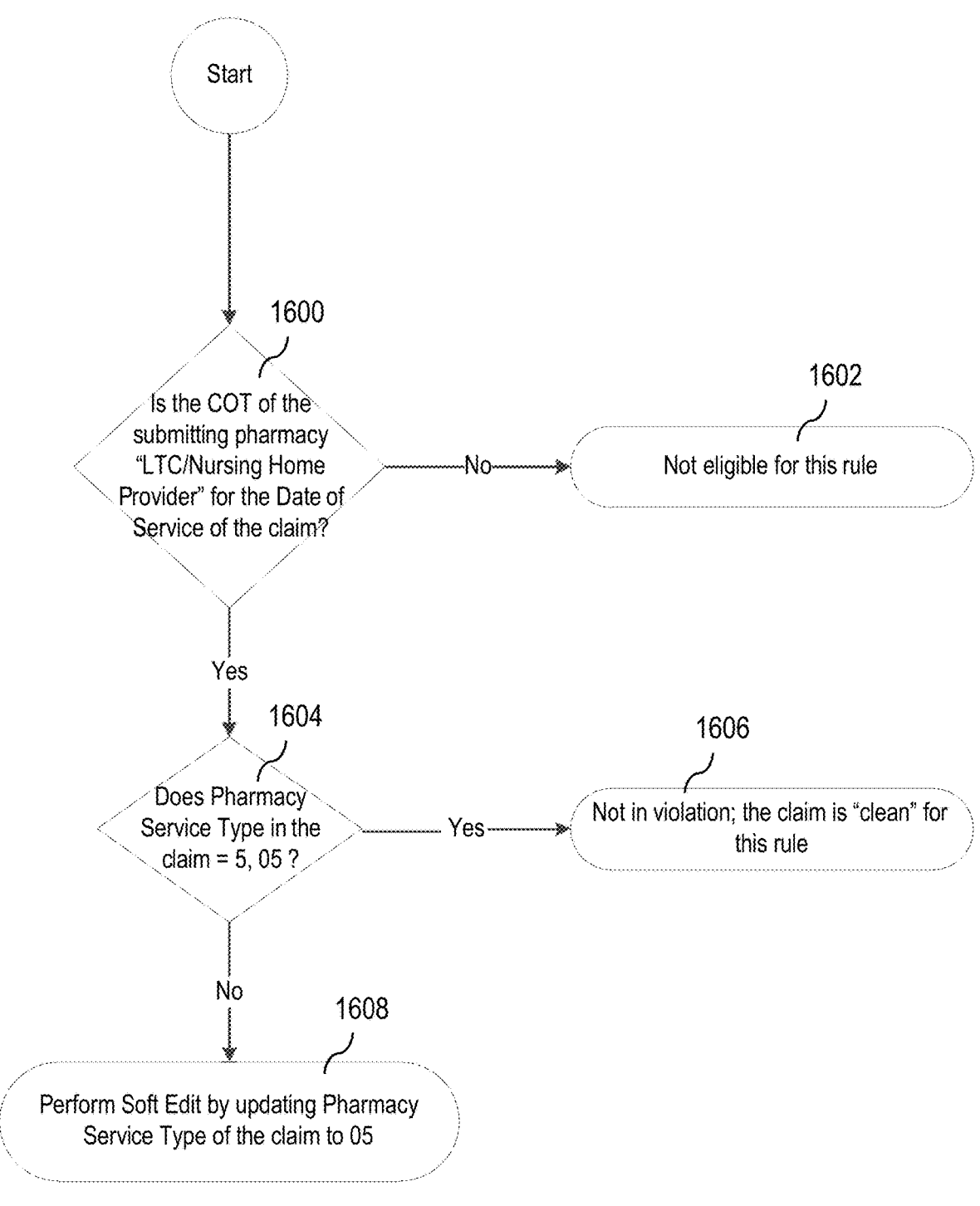
FIGS. 16A-16B are flow charts.

FIG. 16A shows an example of processing, by the rules engine, associated with a pharmacy service type rule.

The rules engine determines whether a class of trade (COT) of a pharmacy submitting a transaction is "LTC/Nursing Home Provider" for the date of service of the transaction (1600). If the result at 1600 is negative, the rules engine determines that the transaction is not eligible for further processing according to the rule (1602).

If the result at 1600 is positive, the rules engine checks whether a pharmacy service type in the transaction matches the "LTC/Nursing Home Provider" categorization (1604), e.g., checks whether the pharmacy service type is "5" or "05." If the result at 1604 is negative, then the rules engine determines that the pharmacy service type field in the transaction is "clean" for this rule (1606). If the result at 1604 is positive, then the rules engine performs an on-the-fly modification to cause the pharmacy service type to match the "LTC/Nursing Home Provider" categorization (1608), e.g., changes the pharmacy service type in the transaction to "5" or "05."

Patient Residence Code

Figure 16B:
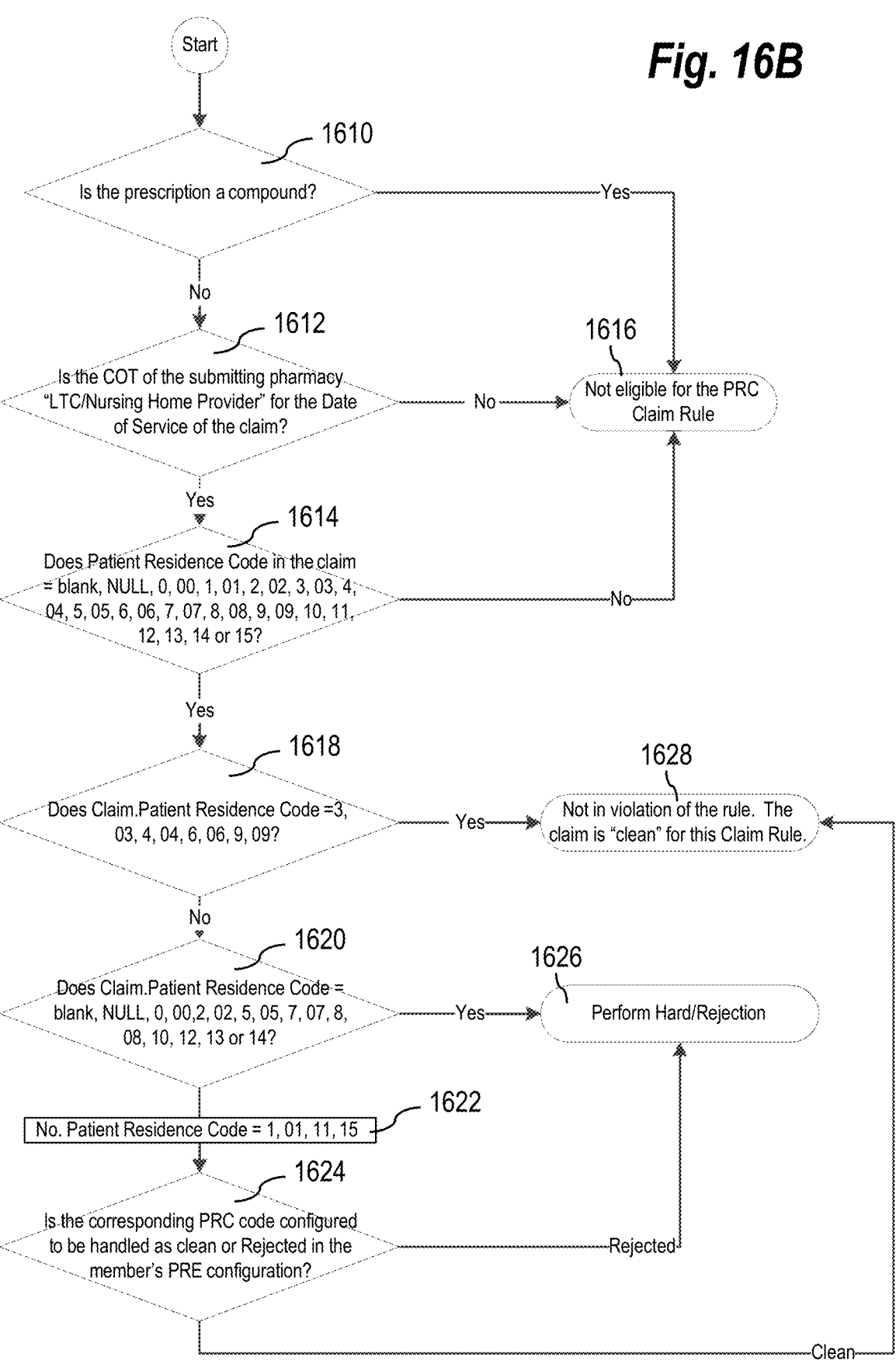

FIG. 16B shows an example of processing, by a rules engine, associated with a patient residence code rule.

The rules engine determines whether the drug dispensed in a received transaction is a compound (1610). The rules engine determine whether a COT of a pharmacy submitting the transaction is "LTC/Nursing Home Provider" for the date of service of the transaction (1612). The rules engine determines a patient residence code in the transaction corresponds to a particular set of residence codes (several possible examples of such a residence code are shown in FIG. 16B).

If the result of 1610 is positive, or the results 1612 or 1614 are negative, the rules engine determines that the received transaction is not eligible for further processing according to the patient residence code rule (1616).

Otherwise, the rules engine determines whether the patient residence code corresponds to another set of residence codes (several possible examples of such a residence code are shown in FIG. 16B) (1618). If the result at 1618 is negative, the rules engine determines whether the patient residence code corresponds to a third set of residence codes (several possible examples of such a residence code are shown in FIG. 16B) (1620). If the result at 1620 is negative, the rules engine determines, that the patient residence code corresponds to a fourth set of residence codes (several possible examples of such a residence code are shown in FIG. 16B) (1622).

The rules engine proceeds to determine whether the pharmacy's rule configurations are such that the determined patient residence code should be handled as clean, or whether the configurations are such that the determined patient residence code should be handled as rejected (1624).

If the code is handled as a rejected, or if the result of 1620 is positive, then the rules engine returns a rejection for the transaction (1626). If the code is handled as clean, or if the result of 1618 is positive, then the rules engine determines that the patient residence code field is clean according to this rule (1628).

The examples of rules-based processing described in reference to FIGS. 10-16B are non-limiting. The rules engine is configurable to, for example, check other transaction fields, modify transaction fields differently, and perform processes in orders other than those described in reference to FIGS. 10-16B. As described above, the rules engine is also configurable to add supplementary information to a wrapper of transactions based on outcomes of rules-based processing.

PIS Updates

According to some embodiments of this disclosure, a rules engine workflow is added to cause updates to PIS-side data, e.g., customer PIS referential data, to aid pharmacies in working off of more up-to-date and accurate information within the PIS. PIS data modification may improve the quality of the data in the customers' (e.g., one pharmacy's or a multi-pharmacy company's) core pharmacy dispensing system across the patient roster. It may also aid in reducing the number of incorrect claims sent out.

When a transaction is processed by the rules engine, the rules engine produces an output that may contain data that has been modified from the input. The rules engine may indicate these modifications in supplementary data added to the transaction wrapper. The rules engine may also, as described above, add other types of supplementary data to the transaction wrapper, e.g., an indication of a need for a clinical intervention or an indication to the PIS to update certain inventory or other data records. Because of the extensible data wrapper, this supplementary data may be included without changing the format of the underlying transaction data, such that the underlying transaction data may be processed by the PIS as usual.

At least some portions of the supplementary data are configured to indicate to the PIS corresponding updates to be performed by the PIS on any relevant elements within the PIS database, e.g., updates elements that were changed by the rules engine with an on-the-fly update. The PIS data that is updated may be specific to a particular patient, drug, or other item stored within the PIS database. The modified data may be utilized by the pharmacy team for future patient management, inventory management, financial management, claims adjudication as well as for other pharmacy operations.

To integrate the supplementary data directly with the PIS' operations, the rules engine configures a format of the supplementary data to make the supplementary data readable and interpretable by the PIS. This may include generating encoded instructions that, when interpreted by the PIS, indicate to the PIS a result of the rules-based processing (e.g., a relative status of a current patient with respect to a statistical distribution of other patients analyzed by the rules engine) or a recommended operation to be performed by the PIS. The rules engine may select an appropriate format for encoded instructions based on pharmacy-specific data stored in the managed cache instance and/or in the PCM.

FIGS. 17A-C provide an example of a process in which a transaction of pharmacy claim data results in PIS-side data updates. It should be noted that, although the example is focused on pharmacy claim data, the techniques described below with reference to FIG. 17A-C can be utilized for processing a wide array of structured data including, but not limited to, electronic health records (EHR), electronic medical records (EMR), and eligibility and financial/accounts receivable (A/R) data. FIG. 17A begins at the approximate point in the workflow where the functionality disclosed herein is initiated. Other upstream processes prior to transaction submission from the PIS are omitted from FIGS. 17A-17C for clarity.

A claim is submitted to the PIS by a submitting pharmacy (1701). A check is made using PIS configuration data to determine whether the submitting pharmacy is a valid user of a rules engine (1702). Depending on the outcome of that check, the transaction advances through subsequent processing to either integrate with the system disclosed herein, or to proceed in a manner without integration with the disclosed system.

If the submitting pharmacy is not a valid user of the rules engine, a Pharmacy Communication Manager (PCM), as described in reference to FIG. 2, processes the claim further, e.g., routes the claim to a switch for conventional processing (1720).

When the submitting pharmacy is a valid user of the rules engine in accordance with the PIS configuration data, the PCM interacts with the rules engine (1703). This interaction may involve real-time bi-directional communication, mediated by the API gateway, between the PCM and a rules processing system, as described in reference to FIG. 2 and throughout this disclosure. The communication may be mediated by an API gateway. All interactions among components throughout the entire process may be achieved technically, for example, using https calls.

Once the transaction is received by the rules processing system, a check is made on the rules engine side to determine if the submitting pharmacy has a valid license key authorizing utilization of the rules engine. Authorized cases proceed. When a valid license key is not found, a communication is sent via the API gateway to the PCM indicating an unauthorized exception.

The transaction is processed by a translation component (sometimes abbreviated as TRN) and by the rules engine, as described in further detail throughout this disclosure. The transaction is processed by the TRN and transferred to the rules engine (1705). The transaction is processed by the rules engine to generate output (1706), including generating supplementary data in a wrapper of the transaction. The TRN re-formats the transaction back to the PIS format (1707).

The transaction is then transmitted back from the rules processing system to the PCM (1708). The PIS executes one or more actions based on the transaction, including based on supplementary data included in the transaction wrapper (1709). Examples of such actions that the PIS may invoke include, without limitation, providing notifications to pharmacy technicians identifying why a transaction is rejected or has been augmented (modified), passing augmented transactions to the switch, updating PIS configuration, updating certain reference data, and initiating work-flows such as creating action items in a queue. In some embodiments, these actions are performed based on interpreting an encoded instruction included in the supplementary data. In some embodiments, the encoded instruction includes a scripted command, and the actions are performed based on converting the scripted command to executable code using an interpreter.

The PIS tests whether the advice to the PIS was rejection (1710).

In some embodiments, if the outcome from the rules engine includes an encoded instruction indicating that the transaction should be advanced (e.g., "advance the transaction to the switch"), or if the transaction is not being rejected, further processing takes place.

The PIS transmits the (in some cases, modified) transaction to the switch (1711). The PIS receives, from the switch and via the PBM, a Promise to Pay (PtP) record (1712).

In some embodiments, the PtP record is processed by the rules engine. For example, additional rules within the rules engine can be applied to the PtP, and the PtP is sent from the PIS to the rules engine, processed at the rules engine (including translation and, in some embodiments, modification), and received back by the PIS, as described throughout this disclosure in reference to transactions in general. The RCM receives the PtP and advances the transaction to the TRN (1713). The TRN translates the PtP to rules engine format and advances the transaction to the rules engine (1714). The rules engine processes the transaction (1715). This processing can include storing the PtP record and passing the PtP back to the TRN. The TRN re-formats the PtP back to PIS specific format and transfers to the API gateway (1716). The API gateway transmits the PtP back to the PCM (1717). Potentially, the rules engine may have generated supplementary data for a wrapper of the PtP data, and this supplementary data, when received by the PIS, may also trigger work-flows and actions in the PIS. The PIS proceeds to process the PtP (1718).

Because the wrapper may be flexibly modified to include a wide variety of data types and a large amount of data without disrupting the format of the underlying transaction (e.g., claim transaction, PtP, or inventory transaction), PIS-side operations triggered by the supplementary data can correspondingly take a variety of forms. For example, rules engine processing that is applied to just one single transaction can trigger a correction or update to large amounts of reference or configuration data in the PIS. This correction/ update may then, in turn, result in some or all subsequent transactions submitted by the same pharmacy or submitted for the same item (e.g., as indicated by the NDC) being baselined with more accurate and updated information, reducing incorrect submissions in the future that may result in reduced or less accurate reimbursement amounts. Because the correction/update is triggered directly by the PIS receiving the supplementary data in the wrapper, the correction/update process is made more efficient.

Other operations that may be triggered by supplementary data in the extensible wrapper include making configuration and referential data updates within the PIS, triggering various work-flows resulting from the rules engine's processing, applying changes to transactions prior to forwarding to a switch, and presenting end-users with useful information such as making recommendations in claims submissions, advising on which updates have been applied, and informing pharmacies of root causes of rejections, based on the results of the processing by the rules engine.

Figure 18:
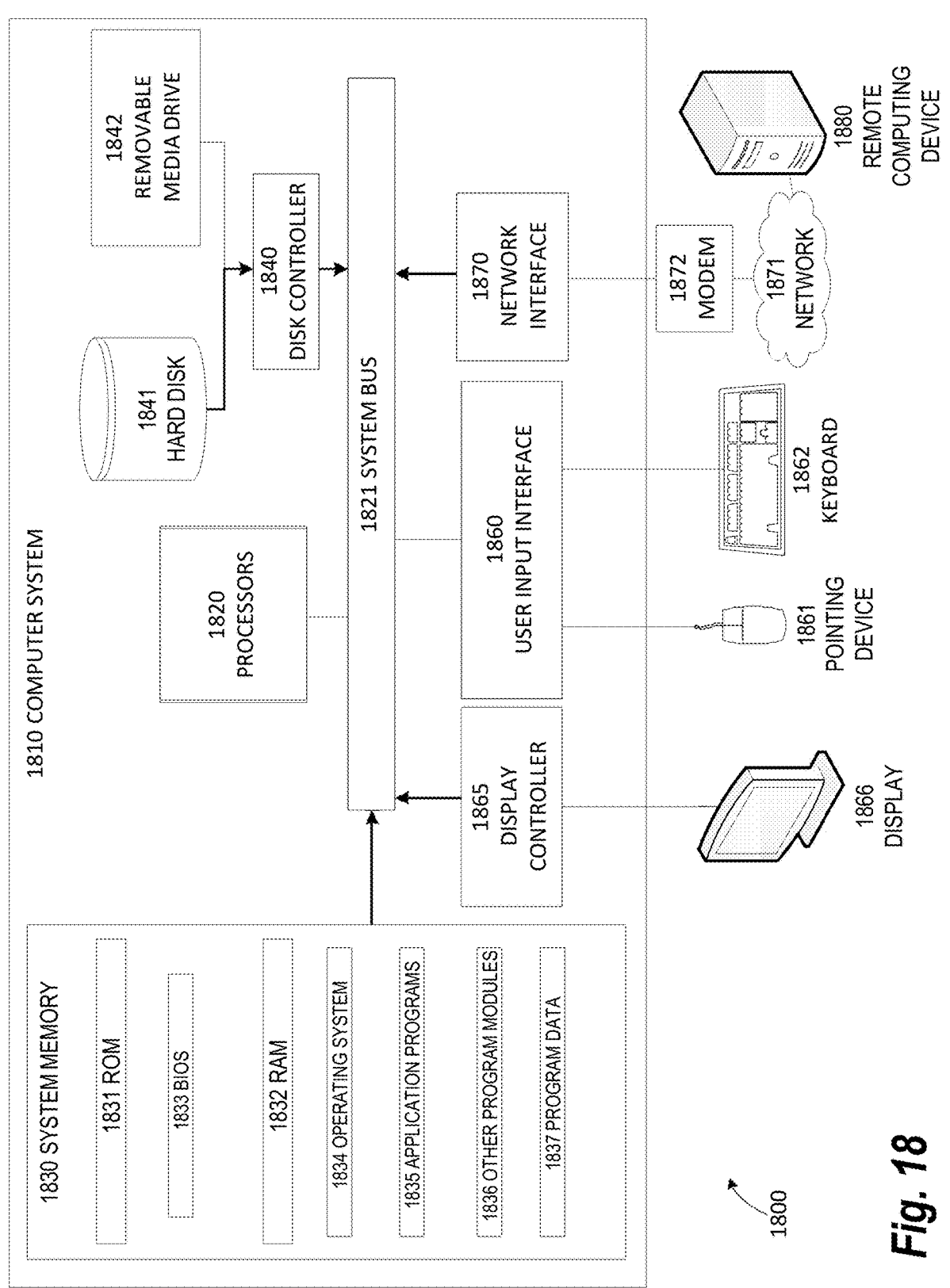
FIG. 18 is a block diagram showing an example system.

FIG. 18 illustrates an exemplary computing environment 1800 within which embodiments according to this disclosure may be implemented. For example, the computing environment 1800 may be used to implement the PCM 200A or rules processing system 200B illustrated FIG. 2. The computing environment 1800 may include computer system 1810, which is one example of a computing system by which embodiments according to this disclosure may be implemented. Computers and computing environments, such as computer system 1810 and computing environment 1800, are known to those of skill in the art and thus are described briefly here.

As shown in FIG. 18, the computer system 1810 may include a communication mechanism such as a bus 1821 or other communication mechanism for communicating information within the computer system 1810. The computer system 1810 further includes one or more processors 1820 coupled with the bus 1821 for processing the information. The processors 1820 may include one or more central processing units (CPUs), graphical processing units (GPUs), or any other processor known in the art. In some embodiments, a cloud-based computing environment may be used for implementing the systems and methods described herein. Techniques such as server virtualization can be used to maximize the use of hardware resources.

The computer system 1810 also includes a system memory 1830 coupled to the bus 1821 for storing information and instructions to be executed by processors 1820. The system memory 1830 may include computer readable storage media in the form of volatile and/or nonvolatile memory, such as read only memory (ROM) 1831 and/or random access memory (RAM) 1832. The system memory RAM 1832 may include other dynamic storage device(s) (e.g., dynamic RAM, static RAM, and synchronous DRAM). The system memory ROM 1831 may include other static storage device(s) (e.g., programmable ROM, erasable PROM, and electrically erasable PROM). In addition, the system memory 1830 may be used for storing temporary variables or other intermediate information during the execution of instructions by the processors 1820. A basic input/output system (BIOS) 1833 containing the basic routines that help to transfer information between elements within computer system 1810, such as during start-up, may be stored in ROM 1831. RAM 1832 may contain data and/or program modules that are immediately accessible to and/or presently being operated on by the processors 1820. System memory 1830 may additionally include, for example, operating system 1834, application programs 1835, other program modules 1836 and program data 1837.

The computer system 1810 also includes a disk controller 1840 coupled to the bus 1821 to control one or more storage devices for storing information and instructions, such as a hard disk 1841 and a removable media drive 1842 (e.g., floppy disk drive, compact disc drive, tape drive, and/or solid state drive). The storage devices may be added to the computer system 1810 using an appropriate device interface (e.g., a small computer system interface (SCSI), integrated device electronics (IDE), Universal Serial Bus (USB), or FireWire).

The computer system 1810 may also include a display controller 1865 coupled to the bus 1821 to control a display 1866, such as a liquid crystal display (LCD) or light emitting diode (LED) monitor, for displaying information to a computer user. The computer system includes an input interface 1860 and one or more input devices, such as a keyboard 1862 and a pointing device 1861, for interacting with a computer user and providing information to the processors 1820. The pointing device 1861, for example, may be a mouse, a trackball, or a pointing stick for communicating direction information and command selections to the processors 1820 and for controlling cursor movement on the display 1866. The display 1866 may provide a touch screen interface which allows input to supplement or replace the communication of direction information and command selections by the pointing device 1861.

The computer system 1810 may perform a portion or all of the processing described in this disclosure in response to the processors 1820 executing one or more sequences of one or more instructions contained in a memory, such as the system memory 1830. Such instructions may be read into the system memory 1830 from another computer readable medium, such as a hard disk 1841 or a removable media drive 1842. The hard disk 1841 may contain one or more datastores and data files used by embodiments of the present disclosure. Datastore contents and data files may be encrypted to improve security. The processors 1820 may also be employed in a multi-processing arrangement to execute the one or more sequences of instructions contained in system memory 1830. In some embodiments, hard-wired circuitry may be used in place of or in combination with software instructions. Thus, embodiments are not limited to any specific combination of hardware circuitry and software.

As stated above, the computer system 1810 may include at least one computer readable medium or memory for holding instructions programmed according to embodiments of this disclosure and for containing data structures, tables, records, or other data described herein. The term "computer readable medium" as used herein refers to any medium that participates in providing instructions to the processor 1820 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1841 or removable media drive 1842. Non-limiting examples of volatile media include dynamic memory, such as system memory 1830. Non-limiting examples of transmission media include coaxial cables, copper wire, and fiber optics, including the wires that make up the bus 1821. Transmission media may also take the form of acoustic or light waves, such as those generated during radio wave and infrared data communications.

The computing environment 1800 may further include the computer system 1810 operating in a networked environment using logical connections to one or more remote computers, such as remote computer 1880. Remote computer 1880 may be a personal computer (laptop or desktop), a mobile device, a server, a router, a network PC, a peer device or other common network node, and typically includes many or all of the elements described above relative to computer system 1810. When used in a networked environment, computer system 1810 may include modem 1872 for establishing communications over a network 1871, such as the Internet. Modem 1872 may be connected to bus 1821 via user network interface 1870, or via another appropriate mechanism.

Network 1871 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1810 and other computers (e.g., remote computer 1880). The network 1871 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1871.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, includes code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, includes one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The embodiments of the figures are not exclusive. Other embodiments may be derived in accordance with this disclosure; the explicitly-described embodiments are for illustration purposes only. Modifications to the disclosed embodiments may be implemented by those skilled in the art. As described herein, the various systems, subsystems, agents, managers, components, and processes can be implemented using hardware components, software components, and/or combinations thereof.

What is claimed is:

1. A rules processing system comprising:
one or more processors, and
one or more memory devices storing non-transitory, computer-readable instructions that, when executed by the one or more processors, cause the one or more processors to perform operations comprising:
receiving, by an application program interface (API) gateway, a transaction from a pharmacy, the transaction having a first data format,
validating, by the API gateway, that the pharmacy is authorized to access the rules processing system,
reformatting, by a translation component, the transaction received by the API gateway into a structured data format used by a rules engine included in the rules processing system,
evaluating, by the rules engine, one or more fields of the transaction according to a configurable set of logic rules, comprising at least one of
modifying values of the one or more fields, generating a rejection of the transaction, or generating an indication that at least some of the one or more fields do not violate the set of logic rules,
inserting, into a wrapper of the transaction, supplementary data based on the evaluation of the one or more fields,
reformatting, by the translation component, the transaction into the first data format, and
transmitting, by the API gateway, the transaction to the pharmacy,
wherein the wrapper comprises an extensible data structure having a plurality of fields, the plurality of fields including metadata of the transaction,
wherein the extensible data structure of the wrapper has a second data format different from the first data format,
wherein the first data format is incompatible with storage of the supplementary data, and
wherein the second data format is compatible with storage of the supplementary data, and
wherein reformatting the transaction into the first data format comprises retaining the wrapper in the second data format.

2. The rules processing system of claim 1, wherein evaluating the one or more fields comprises:
comparing a value in a first field of the one or more fields to a predetermined comparison value;
determining, based on a result of comparing the value to the predetermined comparison value, that a logic rule in the set of logic rules dictates a change to the value; and
changing the value in the first field to a modified value according to the logic rule.

3. The rules processing system of claim 1, wherein the supplementary data comprises an indication of at least one on-the-fly update performed on the transaction by the rules processing system.

4. The rules processing system of claim 1, wherein the supplementary data comprises an encoded instruction indicating one or more other operations to be performed by the pharmacy.

5. The rules processing system of claim 4, wherein the operations comprise:
  accessing stored data indicating a format for the encoded instruction based on the pharmacy from which the transaction is received; and
  generating the encoded instruction in the indicated format.

6. The rules processing system of claim 4, wherein the encoded instruction comprises a scripted command corresponding to executable code that, when executed, causes the one or more other operations to be performed.

7. The rules processing system of claim 4, wherein the wrapper comprises an indication of a format of the encoded instruction.

8. The rules processing system of claim 1, wherein inserting the supplementary data into the wrapper comprises:
  adding a new field to the wrapper; and
  inserting the supplementary data into the new field.

9. The rules processing system of claim 1, wherein the logic rules depend upon a set of pharmacy-specific parameters.

10. The rules processing system of claim 1, wherein the rules processing system comprises a cloud-based system remote from the pharmacy, and wherein the API gateway comprises an internet-accessible API gateway.

11. The rules processing system of claim 1, wherein the operations comprise:
  comparing data in the transaction to stored data from one or more other transactions;
  based on the comparison, generating an indication that a clinical intervention is needed for a patient associated with the transaction; and
  including the indication in the supplementary data.

12. The rules processing system of claim 1, wherein the operations comprise:
  applying a machine learning model to data in the transaction and to data included in one or more other transactions from one or more other pharmacies, to generate an outbreak prediction indicating a predicted disease outbreak; and
  including the outbreak prediction in the supplementary data.

13. A computer-implemented method for transaction processing by a rules processing system, the method comprising:
  receiving, by an application program interface (API) gateway, a transaction from a pharmacy, the transaction having a first data format,
  validating, by the API gateway, that the pharmacy is authorized to access the rules processing system,
  reformatting, by a translation component, the transaction received by the API gateway into a structured data format used by a rules engine included in the rules processing system,
  evaluating, by the rules engine, one or more fields of the transaction according to a configurable set of logic rules, comprising at least one of

36 modifying values of the one or more fields, generating a rejection of the transaction, or generating an indication that at least some of the one or more fields do not violate the set of logic rules,
  inserting, into a wrapper of the transaction, supplementary data based on the evaluation of the one or more fields,
  reformatting, by the translation component, the transaction into the first data format, and
  transmitting, by the API gateway, the transaction to the pharmacy,
  wherein the wrapper comprises an extensible data structure having a plurality of fields, the plurality of fields including metadata of the transaction,
  wherein the extensible data structure of the wrapper has a second data format different from the first data format,
  wherein the first data format is incompatible with storage of the supplementary data, and wherein the second data format is compatible with storage of the supplementary data, and
  wherein reformatting the transaction into the first data format comprises retaining the wrapper in the second data format.

14. The computer-implemented method of claim 13, wherein the supplementary data comprises an encoded instruction indicating one or more operations to be performed by the pharmacy.

15. The computer-implemented method of claim 14, comprising:
  accessing stored data indicating a format for the encoded instruction based on the pharmacy from which the transaction is received; and
  generating the encoded instruction in the indicated format.

16. The computer-implemented method of claim 13, wherein inserting the supplementary data into the wrapper comprises:
  adding a new field to the wrapper; and
  inserting the supplementary data into the new field.

17. A non-transitory, computer-readable medium storing instructions that, when executed by a computer system, cause the computer system to perform operations for transaction processing by a rules processing system, the operations comprising:
  receiving, by an application program interface (API) gateway, a transaction from a pharmacy, the transaction having a first data format,
  validating, by the API gateway, that the pharmacy is authorized to access the rules processing system,
  reformatting, by a translation component, the transaction received by the API gateway into a structured data format used by a rules engine included in the rules processing system,
  evaluating, by the rules engine, one or more fields of the transaction according to a configurable set of logic rules, comprising at least one of
    modifying values of the one or more fields, generating a rejection of the transaction, or generating an indication that at least some of the one or more fields do not violate the set of logic rules,
  inserting, into a wrapper of the transaction, supplementary data based on the evaluation of the one or more fields,
  reformatting, by the translation component, the transaction into the first data format, and
  transmitting, by the API gateway, the transaction to the pharmacy, wherein the wrapper comprises an extensible data structure having a plurality of fields, the plurality of fields including metadata of the transaction, wherein the extensible data structure of the wrapper has a second data format different from the first data format, wherein the first data format is incompatible with storage of the supplementary data, and wherein the second data format is compatible with storage of the supplementary data, and wherein reformatting the transaction into the first data format comprises retaining the wrapper in the second data format.

18. The computer-readable medium of claim 17, wherein the supplementary data comprises an encoded instruction indicating one or more other operations to be performed by the pharmacy.

19. The computer-readable medium of claim 18, wherein the operations comprise:

accessing stored data indicating a format for the encoded instruction based on the pharmacy from which the transaction is received; and generating the encoded instruction in the indicated format.

20. The computer-readable medium of claim 17, wherein inserting the supplementary data into the wrapper comprises:

adding a new field to the wrapper; and inserting the supplementary data into the new field.

\* \* \* \* \*